(12) United States Patent
Clague et al.

(10) Patent No.: US 7,189,231 B2
(45) Date of Patent: Mar. 13, 2007

(54) ELECTROSURGICAL METHODS AND APPARATUS FOR MAKING PRECISE INCISIONS IN BODY VESSELS

(75) Inventors: Cynthia T. Clague, Minnetonka, MN (US); Philip J. Haarstad, Chanhassen, MN (US); Scott E. Jahns, Hudson, WI (US); James R. Keogh, Maplewood, MN (US); Christopher P. Olig, Eden Prairie, MN (US); Raymond W. Usher, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 184 days.

(21) Appl. No.: 10/917,755

(22) Filed: Aug. 13, 2004

(65) Prior Publication Data
US 2005/0033277 A1 Feb. 10, 2005

Related U.S. Application Data

(62) Division of application No. 10/278,966, filed on Oct. 23, 2002, now Pat. No. 6,960,209.

(51) Int. Cl.
*A61B 18/18* (2006.01)

(52) U.S. Cl. .......................................... 606/45; 606/41

(58) Field of Classification Search .................. 606/41, 606/42, 45–47, 185, 167
See application file for complete search history.

(56) References Cited

U.S. PATENT DOCUMENTS

| | | | |
|---|---|---|---|
| 5,385,606 A | 1/1995 | Kowanko | 106/124 |
| 5,452,733 A | 9/1995 | Sterman et al. | 128/898 |
| 5,464,447 A | 11/1995 | Fogarty et al. | 607/129 |
| 5,695,504 A | 12/1997 | Gifford, III et al. | 606/153 |
| 5,707,380 A | 1/1998 | Hinchiffe et al. | 606/153 |
| 5,716,392 A | 2/1998 | Bourgeois et al. | 607/132 |
| 5,776,154 A | 7/1998 | Taylor et al. | 606/167 |
| 5,799,661 A | 9/1998 | Boyd et al. | 128/898 |
| 5,830,224 A | 11/1998 | Cohn et al. | 606/167 |
| 5,868,770 A | 2/1999 | Rygaard | 606/167 |
| 5,875,782 A | 3/1999 | Ferrari et al. | 128/898 |
| 5,893,369 A | 4/1999 | LeMole | 606/184 |
| 5,904,679 A | 5/1999 | Clayman | 606/39 |
| 5,972,017 A | 10/1999 | Berg et al. | 606/198 |
| 5,976,069 A | 11/1999 | Navia et al. | 600/37 |
| 5,976,178 A | 11/1999 | Goldsteen et al. | 623/1 |
| 6,026,814 A | 2/2000 | LaFontaine et al. | 128/898 |
| 6,068,637 A | 5/2000 | Popov et al. | 606/159 |
| 6,071,295 A | 6/2000 | Takahashi | 606/191 |
| 6,080,175 A | 6/2000 | Hogendijk | 606/185 |

(Continued)

*Primary Examiner*—Roy D. Gibson
(74) *Attorney, Agent, or Firm*—Mike Jaro; Jeffrey J. Hohenshell

(57) ABSTRACT

Methods and apparatus employed in surgery involving making precise incisions in vessels of the body, particularly cardiac blood vessels in coronary revascularization procedures conducted on the stopped or beating heart are disclosed. Such incisions are created by applying an elongated electrosurgical cutting electrode to the outer surface of the vessel wall in substantially parallel alignment with the body vessel axis, the elongated electrosurgical cutting electrode having a predetermined cutting electrode length exceeding the cutting electrode width. RF energy is applied between the electrosurgical cutting electrode and the ground electrode at an energy level and for a duration sufficient to cut an elongated slit through the vessel wall where the elongated electrosurgical cutting electrode is applied to the surface of the vessel wall.

22 Claims, 31 Drawing Sheets

U.S. PATENT DOCUMENTS

| | | | |
|---|---|---|---|
| 6,099,542 A | 8/2000 | Cohn et al. | 606/167 |
| 6,120,436 A | 9/2000 | Anderson et al. | 600/201 |
| 6,231,565 B1 | 5/2001 | Tovey et al. | 606/1 |
| 6,248,117 B1 | 6/2001 | Blatter | 606/153 |
| 6,270,516 B1 | 8/2001 | Tanner et al. | 606/213 |
| 6,331,158 B1 | 12/2001 | Hu et al. | 600/232 |
| 6,332,468 B1 | 12/2001 | Benetti | 128/898 |
| 6,371,964 B1 | 4/2002 | Vargas et al. | 606/153 |
| 6,858,027 B2 * | 2/2005 | Redtenbacher et al. | 606/48 |

* cited by examiner

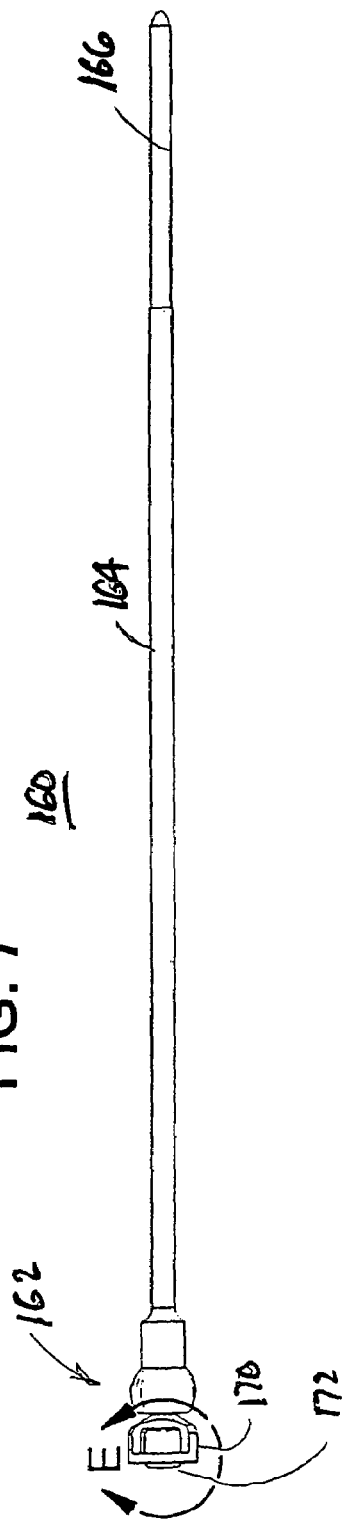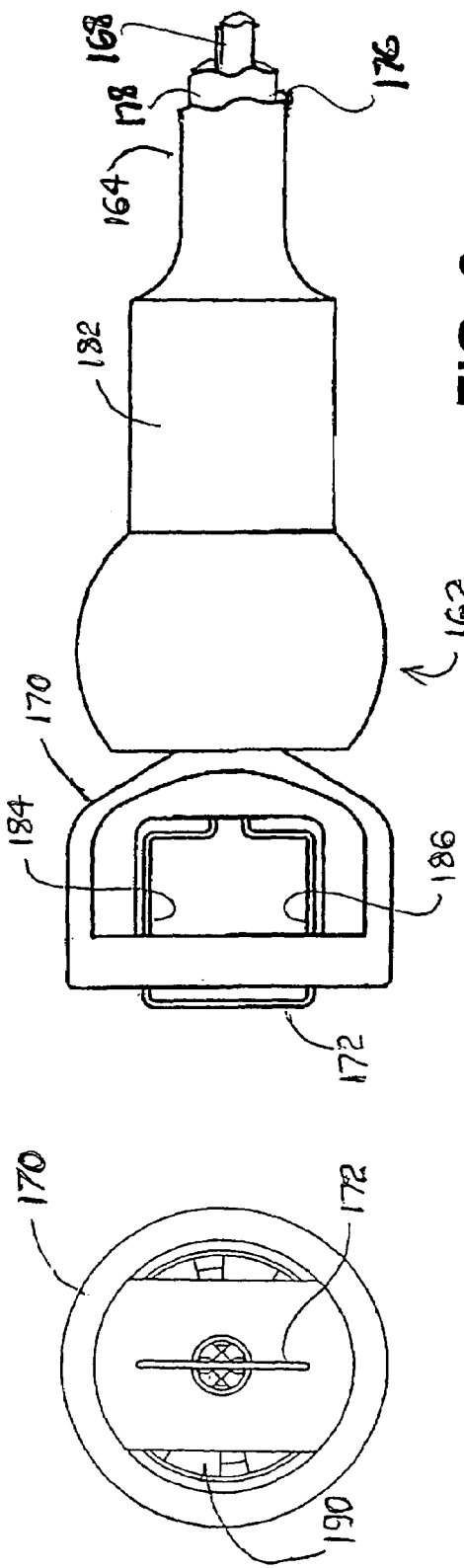
FIG. 7
FIG. 8
FIG. 9

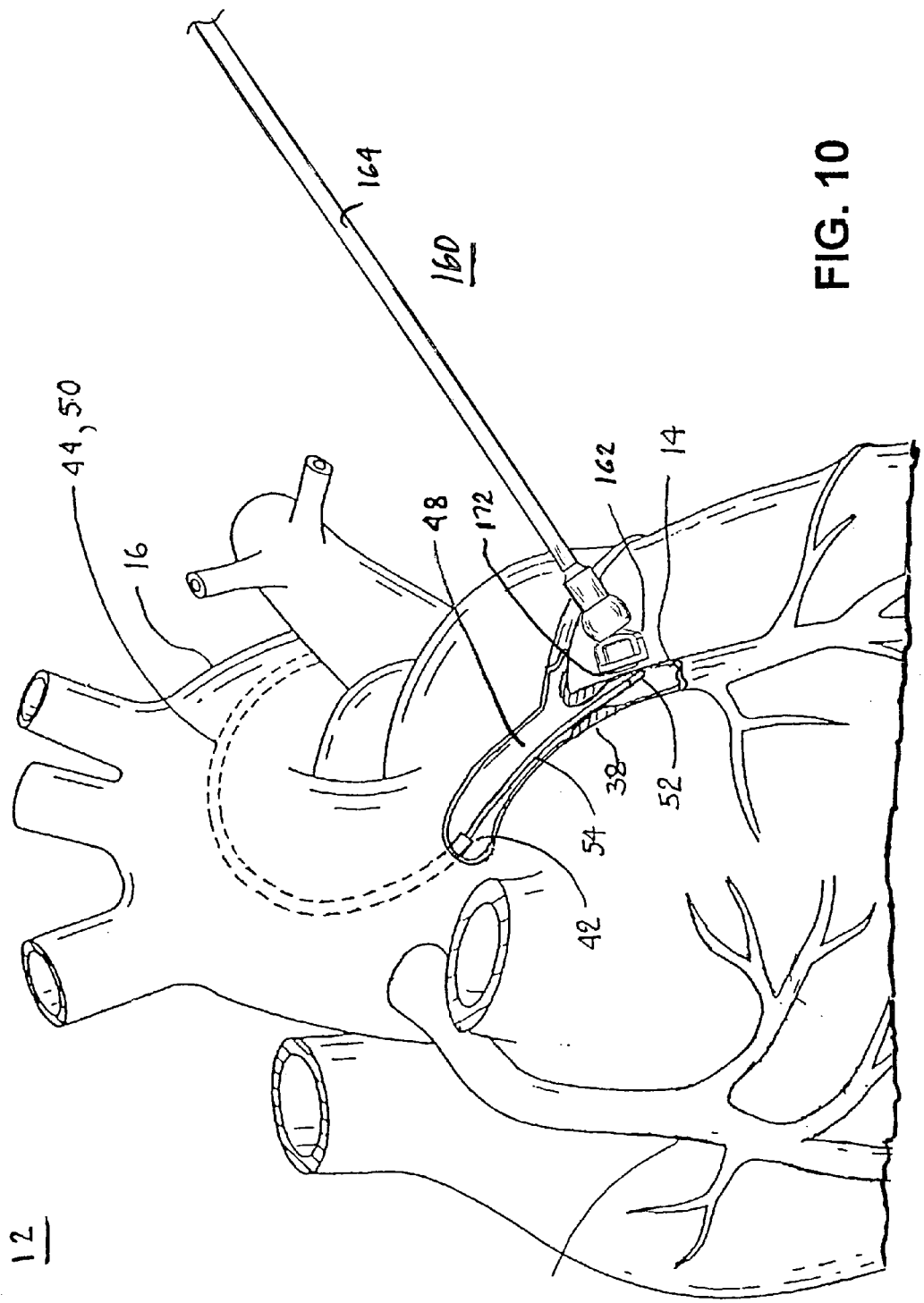

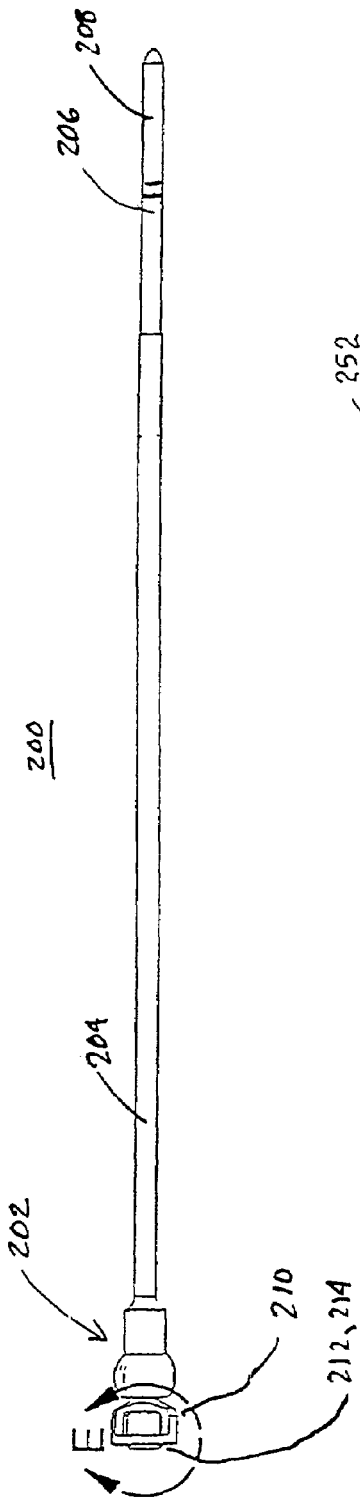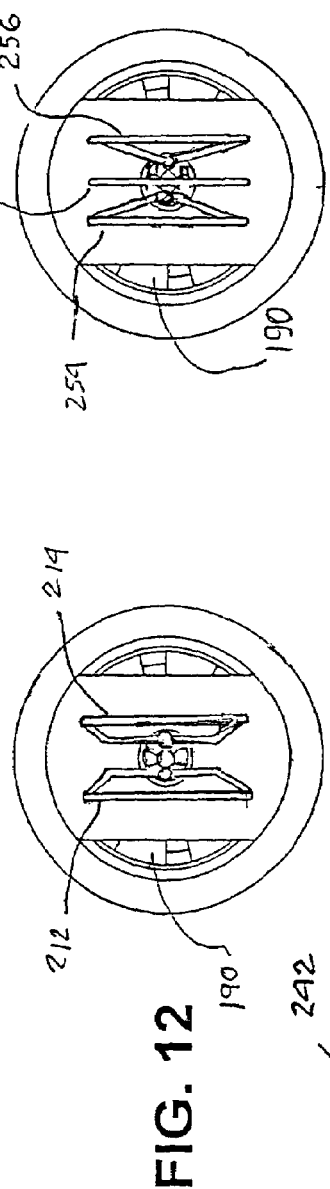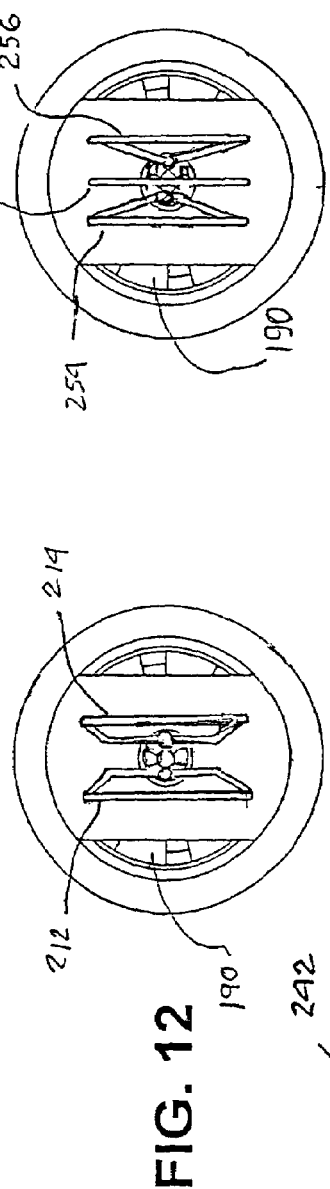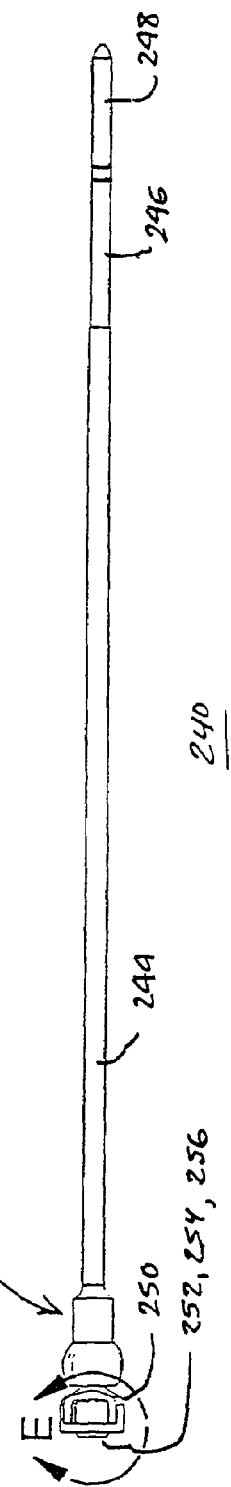

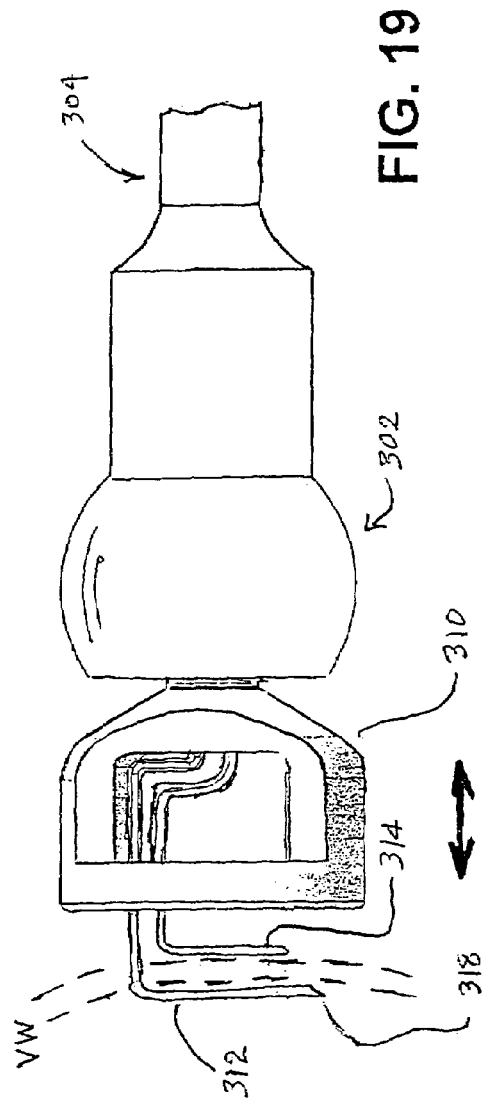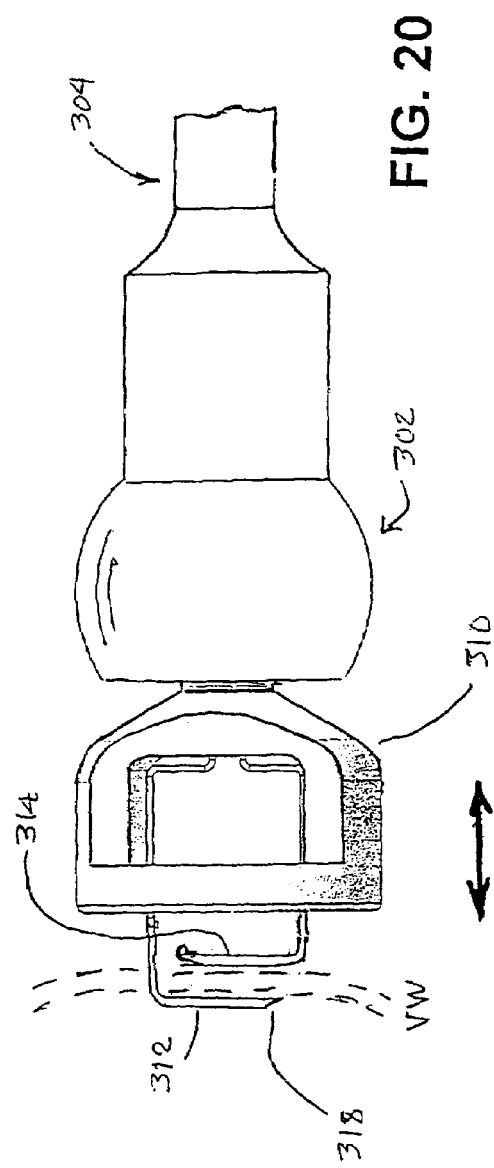

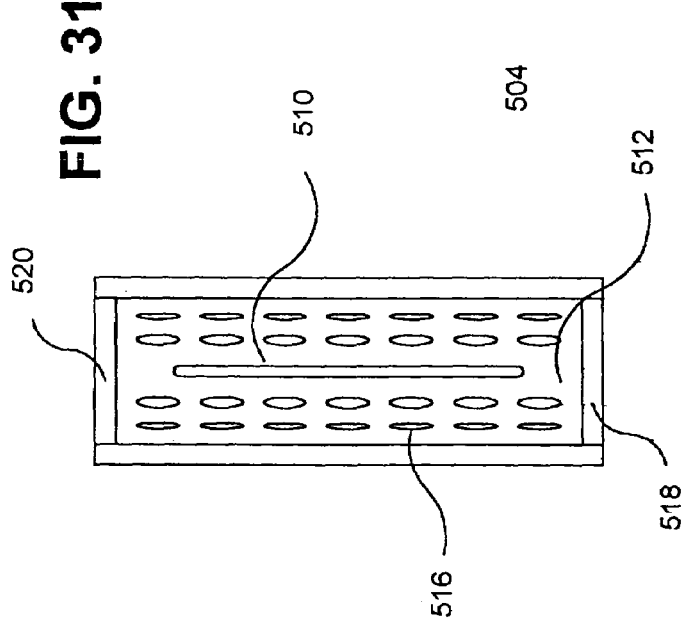
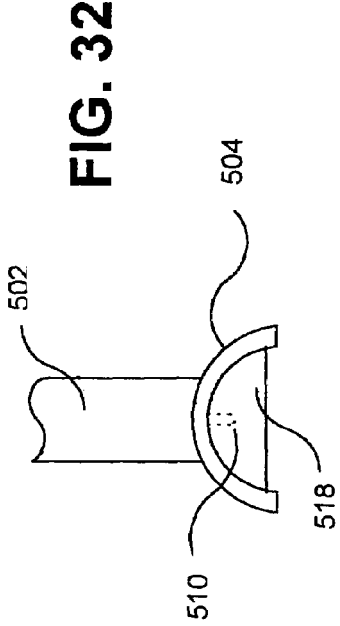
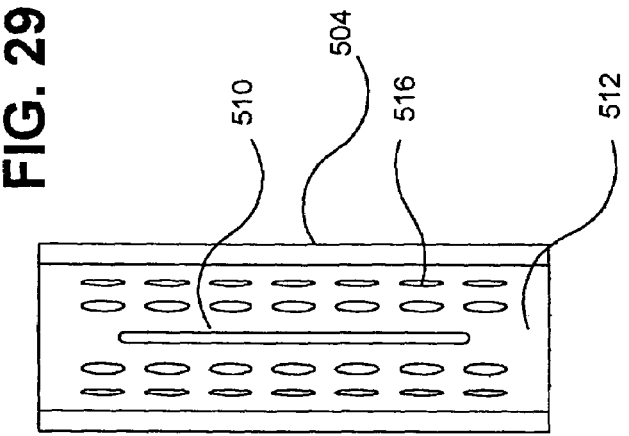
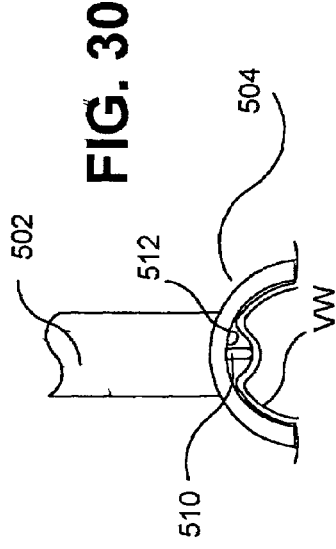

ELECTROSURGICAL METHODS AND APPARATUS FOR MAKING PRECISE INCISIONS IN BODY VESSELS

This application is a divisional of U.S. patent application Ser. No. 10/278,966, ELECTROSURGICAL METHODS AND APPARATUS FOR MAKING PRECISE INCISIONS IN BODY VESSELS, filed Oct. 23, 2002, now U.S. Pat. No. 6,960,209.

FIELD OF THE INVENTION

The present invention pertains to methods and apparatus employed in surgery involving making precise incisions in vessels of the body, particularly cardiac blood vessels in coronary revascularization procedures conducted on the stopped or beating heart.

BACKGROUND OF THE INVENTION

Diseases of the cardiovascular system affect millions of people each year and are a leading cause of death throughout the world. The cost to society from such diseases is enormous both in terms of the number of lives lost as well as in terms of the costs associated with treating patients through traditional surgical techniques. A particularly prevalent form of cardiovascular disease is caused by atherosclerosis, a form of arteriosclerosis.

Atherosclerosis is a disease in which the lumen (interior passage) of an artery becomes stenosed (narrowed) or even totally occluded (blocked) by an accumulation of fibrous, fatty, or calcified tissue. Over time this tissue, known in medicine as an atheroma, hardens and occludes the artery. The partial stenosis or full occlusion of the coronary arteries that supply the heart muscle leads to ischemia (deficient blood flow) of the heart muscle, angina (chest pain), and can lead to infarction (heart attack) or patient death. Although drug therapies and modifications to diet and lifestyle show great promise for preventing and treating atherosclerotic vascular disease, many patients urgently require restoration of blood flow that has already been lost, especially in those having severely or totally occluded blood vessels.

In many cases, a patient suffering a coronary vessel obstruction or restriction undergoes a coronary artery bypass graft (CABG) surgical procedure, more commonly known as a "heart bypass" operation to restore normal oxygenated blood flow to the heart muscle downstream of the obstruction or restriction. More particularly, a fluid connection or "distal anastomosis." is surgically established between a source vessel of oxygenated blood and the obstructed or restricted target coronary artery downstream or distal to the obstruction or restriction to restore the flow of oxygenated blood to the heart muscle. In one approach, the surgeon attaches an available source vessel, e.g., an internal mammary artery (IMA), directly to the obstructed target coronary artery at the distal anastomosis site downstream from the obstruction or restriction.

There are a number of alternative approaches to CABG surgery. In one approach, the surgeon harvests a graft blood vessel from the patient's venous system and prepares its proximal and distal ends to be attached in a "proximal anastomosis" and a "distal anastomosis" bypassing the occlusion. This type of graft is commonly known as a "free" graft. The proximal anastomosis can be located proximal or upstream to the occlusion or to another vessel supplying oxygenated blood, e.g., the aorta. Typically, a section of the saphenous vein is harvested from the patient's body. Sometimes, the internal mammary artery (IMA) is used as the graft blood vessel or the radial artery is used as arterial conduit and the proximal anastomosis has to be made. In another approach, artery-to-artery bypass procedures have been utilized in which an arterial source of oxygenated blood, e.g., the left IMA or right IMA, is severed and a portion is dissected away from supporting tissue so that the severed end can be anastomosed to the obstructed coronary artery distally to the stenosis or occlusion. More recently, other arteries have been used in such procedures, including the inferior epigastric arteries and gastroepiploic arteries. It is also stated in U.S. Pat. No. 6,080,175 that a conventional electrosurgical instrument can be introduced through a port or incision and used to dissect and prepare the bypass graft vessel for coronary anastomosis while viewing the procedure through a thoracoscope.

It is necessary to access and prepare the site or sites of the vessel wall of the target coronary artery where the proximal arid/or distal anastomosis is to be completed and to then make the surgical attachments of the blood vessels. First, it is necessary to isolate the anastomosis site of the target coronary artery from the epicardial tissues and overlying fatty layers. Typically, blunt, rounded #15 scalpel blades are employed to dissect these tissues and layers away from the target coronary artery.

Generally, blood flow in the target coronary artery is interrupted by, for example, temporary ligation or clamping of the artery proximal and distal of the anastomosis site, and the target coronary artery wall is opened to form an arteriotomy, that is, an elongated incision at the anastomosis site extending parallel to the axis of the coronary vessel and equally spaced from the sides of the coronary artery that are still embedded in or against the epicardium. The arteriotomy is typically created by use of a very sharp, pointed, #11 scalpel blade to perforate the coronary artery wall, and the puncture is elongated the requisite length using scissors. A "perfect arteriotomy" is an incision that has straight edges, that does not stray from the axial alignment and equal distance from the sides of the coronary artery, and is of the requisite length.

Similarly, it is necessary to prepare the attachment end of the source vessel by cutting the source vessel end at an appropriate angle for an end-to-side or end-to-end anastomosis or by forming an elongated arteriotomy in the source vessel wall of a suitable length that is axially aligned with the source vessel axis for a side-to-side anastomosis. Typically, the surgeon uses surgical scalpels and scissors to shape the source vessel end or make the elongated arteriotomy slit in the source vessel, and uses sutures or clips to close the open severed end.

In the example depicted schematically in FIG. 1, the heart 12 is prepared as described above for an end-to-side anastomosis of the surgically freed, severed, and appropriately shaped vessel end 31 of the left IMA 30 branching from the aorta 16 and left subclavian artery 18 to the prepared arteriotomy 15 in the vessel wall of the left anterior descending (LAD) coronary artery 14 downstream from the obstruction 38. Similarly, in the example depicted schematically in FIG. 3, the heart 12 is prepared as described above for a side-to-side anastomosis of the left IMA 30 to the prepared arteriotomy 15 in the vessel wall of the LAD coronary artery 14. In the side-to-side anastomosis, an arteriotomy 33 is made in the freed segment of the left IMA 30, and the vessel end 31 is sutured closed.

The prepared end or elongated arteriotomy of the bypass graft or source vessel is attached or anastomosed to the target coronary artery at the arteriotomy in a manner that prevents leakage of blood employing sutures, staples, surgical adhesives and/or various artificial anastomosis devices. For example, an end-to-side anastomosis 35 of the shaped vessel end 31 of the left IMA 30 to the prepared arteriotomy 15 in the vessel wall of the LAD coronary artery 14 is illustrated in FIG. 2. And a side-to-side anastomosis 37 joining the arteriotomy 33 of the left IMA 30 to the prepared arteriotomy 15 of the LAD coronary artery 14 is illustrated, for example, in FIG. 4.

The inner, endothelial layer, vessel linings are less thrombogenic than the outer epithelial layers of blood vessels. So, in one approach, the attachment is made by everting and applying the interior linings of the bypass graft or source vessel and the target coronary artery against one another and suturing or gluing or otherwise attaching the interior linings together. Various types of artificial biocompatible reinforcement sleeves or rings, e.g., those shown in the above-referenced '369 patent can also be used in the anastomosis. Currently, a number of mechanical anastomotic devices, materials, techniques, and procedures are being developed for facilitating the process of forming an anastomosis including vascular clips or staplers, glues, adhesives or sealants, laser welding, mechanical couplers, stents and robot-assisted suturing. These techniques are being developed for performing end-to-end, end-to-side and/or side-to-side anastomoses with or without temporary blood flow interruption. In general, these techniques can include the use of various biomaterials and/or biocompatible agents. See, for example, U.S. Pat. Nos. 5,385,606, 5,695,504, 5,707,380, 5,972,017 and 5,976,178, and 6,231,565.

Various examples of forming the target vessel arteriotomy or arteriotomies, the shaped end or side wall arteriotomy of the source vessel, and the positioning and attachment of the source vessel and target artery together are set forth in U.S. Pat. Nos. 5,776,154, 5,799,661, 5,868,770, 5,893,369, 6,026,814, 6,071,295, 6,080,175, 6,248,117, 6,331,158, and 6,332,468.

In a conventional bypass graft or CABG procedure, the surgeon exposes the obstructed coronary vessel through an open chest surgical exposure or thoracotomy providing direct visualization and access to the epicardium. Typically, fat layers that make it difficult to see either the artery or the occlusion cover the epicardial surface and the obstructed cardiac artery. However, surgeons are able to dissect the fat away to expose the artery and manually palpate the heart to feel the relatively stiff or rigid occlusion within the artery as a result of their training and experience. The surgeon can determine the location and length of the occlusion as well as suitable sites of the target coronary artery for the proximal and distal anastomoses with some degree of success.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire hooks to keep the severed sternum together. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many invasive surgical techniques and devices have been introduced In order to reduce the risk of morbidity, expense, trauma, patient mortality, infection, and other complications associated with open chest cardiac surgery. Less traumatic limited open chest techniques using an abdominal (sub-xyphoid) approach or, alternatively, a "Chamberlain" incision (an approximately 8 cm incision at the sternocostal junction), have been developed to lessen the operating area and the associated complications. In recent years, a growing number of surgeons have begun performing CABG procedures performed while the heart is still beating using minimally invasive direct coronary artery bypass grafting (MIDCAB) surgical techniques and devices. Using the MIDCAB method, the heart typically is accessed through a mini-thoracotomy (i.e., a 6 to 8 cm incision in the patient's chest) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through sleeves or ports inserted in the incisions, and a thoracoscope to view the accessed cardiac site while the procedure is performed as shown, for example, in the above-referenced '175, '295, '468 and '661 patents and in U.S. Pat. Nos. 5,464,447, and 5,716,392. Surgical trocars having a diameter of about 3 mm to 15 mm are fitted into lumens of tubular trocar sleeves or ports, and the assemblies are inserted into skin incisions. The trocar tip is advanced to puncture the abdomen or chest to reach the pericardium, and the trocar is then withdrawn leaving the port in place. Surgical instruments and other devices such as fiber optic thoracoscopes can be inserted into the body cavity through the port lumens. As stated in the '468 patent, instruments advanced through trocars can include electrosurgical tools, graspers, forceps, scalpels, electrocautery devices, clip appliers, scissors, etc.

In the above-described procedures, the surgeon can stop the heart by utilizing a series of internal catheters to stop blood flow through the aorta and to administer cardioplegia solution. The endoscopic approach utilizes groin cannulation to establish cardiopulmonary bypass (CPB) and an intraaortic balloon catheter that functions as an internal aortic clamp by means of an expandable balloon at its distal end used to occlude blood flow in the ascending aorta. A full description of an example of one preferred endoscopic technique is found in U.S. Pat. No. 5,452,733, for example.

However, recently developed, beating heart procedures eliminate the need for any form of CPB, the extensive surgical procedures necessary to connect the patient to a CPB machine, and to stop the heart. A number of surgical instruments have been developed that attempt to stabilize or immobilize a portion of the beating heart that supports the target coronary artery and the anastomosis site. These beating heart procedures described, for example, in the above-referenced '158, '175, '770, '782, and '295 patents and in U.S. Pat. Nos. 5,976,069, and 6,120,436, can be performed on a heart exposed in a full or limited thoracotomy or accessed percutaneously.

For example, a retractor assembly disclosed in the above-referenced '158 patent mounts to and maintains the chest opening while supporting a stabilizer assembly that extends parallel stabilizer bars against the epicardium alongside the target coronary artery so that force is applied across the anastomosis site to suppress heart motion. The surgeon employs conventional manually applied clamps to block blood flow through the arterial lumen and scalpels and scissors to make the elongated incision of the arteriotomy.

Instruments are disclosed in the above-referenced '295 patent that apply suction to the epicardial surface around or alongside the anastomosis site to suppress heart motion. Again, the surgeon employs the conventional manually applied clamps to block blood flow through the arterial lumen and a scalpel to make the elongated incision of the arteriotomy.

Instruments that combine the application of suction to the epicardial surface around or alongside the anastomosis site to suppress heart motion with a cutting mechanism for making the arteriotomy are disclosed in the above-referenced '175 and '770 patents. The surgical cutting instruments disclosed in the '770 and '175 patents include an elongated shaft having a proximal end, a distal end adapted for percutaneous insertion against the target coronary artery over the anastomosis site, and an axial lumen therebetween. A suction pad is formed at the distal end of the shaft, and a cutting element disposed within the lumen of the shaft near the distal end. A vacuum line is fluidly coupled to the lumen of the shaft and is adapted to connect to a vacuum source to effect a suction force at the distal end of the shaft. A control mechanism is provided to selectively block flow between the vacuum source and the lumen. The control mechanism may include a slide valve, an on/off button, or other equivalent mechanism for selectively closing and opening the vacuum pathway. A gripper assembly configured to grip a portion of the coronary artery is also disclosed in the '175 patent.

The cutting element and the shaft are relatively moveable between a retracted position and a cutting position. The cutting element is adapted to make the elongated slit of the arteriotomy in alignment with the axis of the coronary artery when the cutting element and the shaft are in the cutting position and the vacuum holds the anastomosis site steady.

The distal end of the shaft disclosed in the '175 patent has an outside diameter of less than about 5 mm, and the cutting element comprises at least one cutting element having a substantially straight blade cutting edge. The cutting edge is displaced at an angle of between about 15 to 30 degrees relative to a vertical axis through the cutting element. In one embodiment, the cutting element is fixed to an actuator push rod located within the lumen of the shaft, and connected to an actuator, preferably an actuator button, at a proximal end thereof. In another embodiment, the shaft is slidably mounted to a handle of the cutting instrument. An anchor, preferably a rigid rod coaxially disposed within the shaft, fixes the cutting element to the handle. An actuator member mounted to the shaft and biased by a spring is actuated to slide the shaft between retracted and cutting positions with respect to the cutting element.

Additionally or alternatively, at least one electrode may be disposed near the distal end of the shaft to effect or enhance cutting. The electrode may be operatively coupled to the cutting element, preferably substantially co-linearly coupled to the cutting edge. In the depicted embodiments, the electrode extends to the sharpened tip of the cutting element opposite to the cutting blade. In use, the end of the electrode at the tip of the cutting element is placed against the coronary artery and energized by radio frequency energy as the cutting element is moved to the cutting position to facilitate making a small point incision or pilot hole in the coronary artery. Then, the cutting blade is fully advanced to make the elongated cut. Ultrasonic energy may be applied to the cutting element to effect or enhance cutting by the ultrasonically vibrating the cutting blade.

All of the above-described approaches employ a cutting blade to make the elongated slit of the arteriotomy. In most cases, the shaft must be carefully moved to advance the cutting blade along the length of the vessel wall without inadvertently pushing the tip of blade across the vessel lumen and through the vessel wall opposite to the intended slit. Damage can be caused to the vessel wall if care is not taken.

A vessel wall cutting instrument or tool is needed for making an arteriotomy or a similar slit in a vessel wall is needed that avoids or minimizes the need to move the cutting tool or the cutting blade along the vessel wall to slit the vessel wall to a desired length.

A vessel wall cutting instrument or tool is needed that does not inadvertently advance across the vessel wall from the slit and damage the vessel wall opposite to the slit.

A vessel wall cutting instrument or tool is needed that enables occlusion of the blood vessel to inhibit blood loss through the incision as the incision is being made.

A vessel wall cutting instrument is also needed that can make a clean straight incision of predetermined length and width in a vessel wall quickly within the time between heart contractions.

SUMMARY OF THE INVENTION

The present invention is preferably embodied in electrosurgical methods and apparatus for making precise elongated incisions or slits extending lengthwise along and through a vessel wall, e.g., arteriotomy incisions or slits in coronary arteries and source vessels.

In accordance with one aspect of the present invention a method and apparatus for performing the method of making an elongated slit through the vessel wall and into the lumen of a body vessel, having a body vessel axis, of a patient comprises accessing the outer surface of the vessel wall, applying a ground electrode in contact with the body of the patient, applying an elongated electrosurgical cutting electrode to the outer surface of the vessel wall in substantially parallel alignment with the body vessel axis, the elongated electrosurgical cutting electrode having a predetermined cutting electrode length exceeding the cutting electrode width, and applying RF energy between the electrosurgical cutting electrode and the ground electrode at an energy level and for a duration sufficient to cut an elongated slit through the vessel wall where the elongated electrosurgical cutting electrode is applied to the outer surface of the vessel wall.

The present invention advantageously provides plurality of unipolar and bipolar electrosurgical vessel wall cutting instruments or tools for making an arteriotomy or a similar slit in a vessel wall that avoid or minimize the need to move the cutting blade either along the vessel wall to slit the vessel wall to a desired length and that do not inadvertently advance across the vessel wall from the slit and damage the vessel wall opposite to the slit.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 7 is a side view of a first preferred embodiment of a unipolar electrosurgical vessel wall cutting tool of the present invention;

FIG. 8 is an expanded end view in partial cross-section of the distal portion of the unipolar electrosurgical vessel wall cutting tool of FIG. 7;

FIG. 9 is an expanded side view of the distal portion of the unipolar electrosurgical vessel wall cutting tool of FIG. 7;

FIG. 10 is a schematic illustration of the application of the electrosurgical instrument cutting electrode of the unipolar electrosurgical vessel wall cutting tool of FIG. 7 to the exterior vessel wall of a coronary artery and a ground electrode within the arterial lumen to form an arteriotomy in the vessel wall;

FIG. 11 is a side view of a first preferred embodiment of a bipolar electrosurgical vessel wall cutting tool of the present invention;

FIG. 12 is an expanded end view of the distal portion of the bipolar electrosurgical vessel wall cutting tool of FIG. 11;

FIG. 13 is a side view of a first preferred embodiment of a bipolar electrosurgical vessel wall cutting tool of the present invention;

FIG. 14 is an expanded end view of the distal portion of the bipolar electrosurgical vessel wall cutting tool of FIG. 13;

FIG. 19 is an expanded side view of a first variant of the distal portion of the bipolar electrosurgical vessel wall cutting tool of FIG. 18;

FIG. 20 is an expanded side view of a second variant of the distal portion of the bipolar electrosurgical vessel wall cutting tool of FIG. 18;

FIG. 29 is an end view of the electrode head of the electrosurgical vessel wall cutting tool of FIG. 28;

FIG. 30 is partial side view of the electrode head of the electrosurgical vessel wall cutting tool of FIG. 28 applied against a vessel wall;

FIG. 31 is an end view of a variation of the electrode head of the electrosurgical vessel wall cutting tool of FIG. 28;

FIG. 32 is partial side view of the electrode head of the electrosurgical vessel wall cutting tool of FIG. 31;

DETAILED DESCRIPTION OF THE PREFERRED EMBODIMENTS

Figure 1:
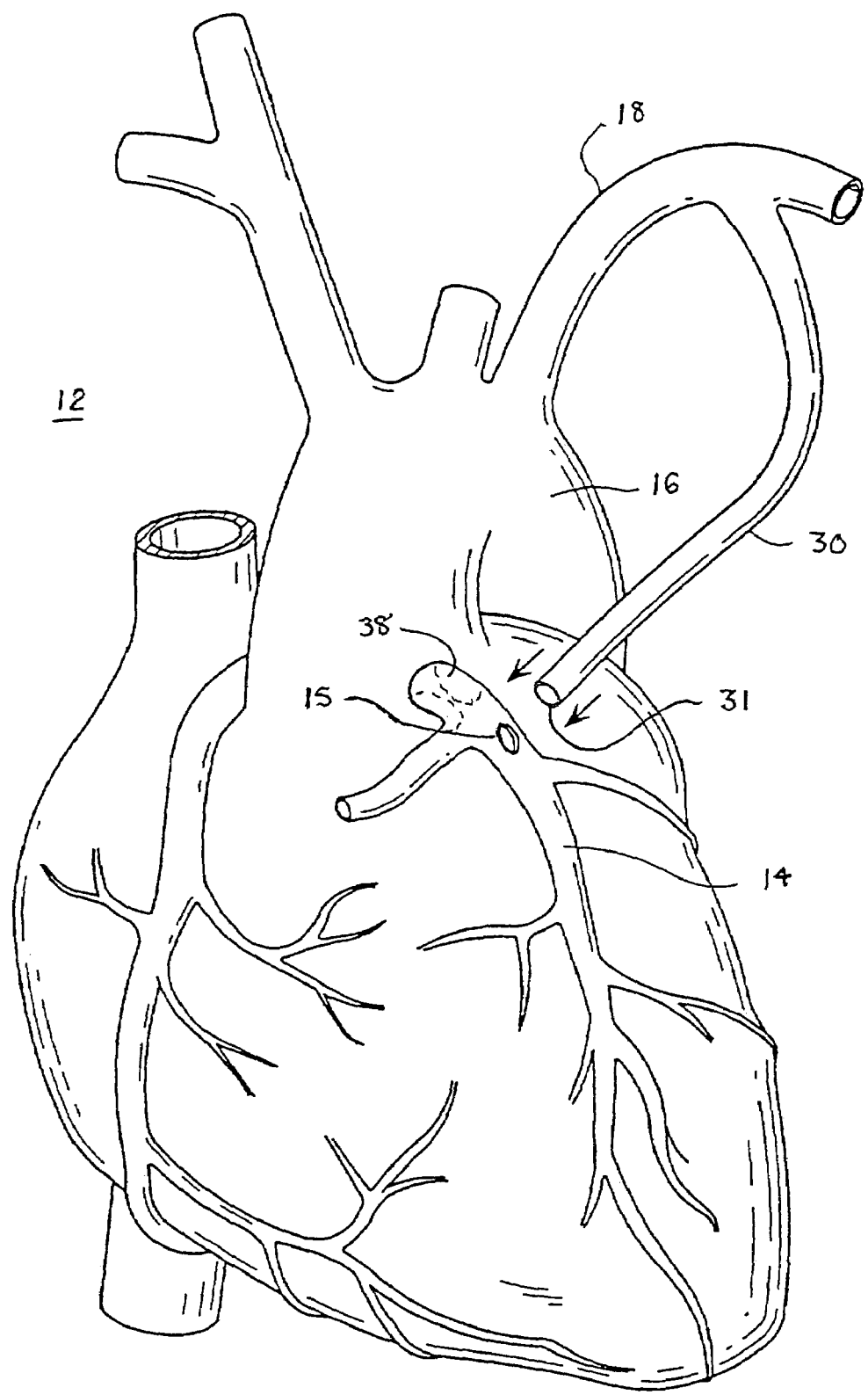
FIG. 1 is a schematic illustration of the preparation of a source vessel free end and an arteriotomy in a coronary artery downstream from an obstruction for an end-to-side anastomosis.

In the following detailed description, references are made to illustrative embodiments for carrying out the invention. It is understood that other embodiments may be utilized without departing from the scope of the invention.

For example, while a preferred method of forming arteriotomies in a coronary artery and a source vessel in the process of performing a coronary artery anastomosis in a thoracoscopic CABG procedure will be described herein, it is to be understood that the principles of the present invention may be applied to a wide variety of surgical procedures, both conventional, open chest procedures, as well as minimally invasive, closed chest procedures, to form precise elongated slits in vessel walls.

Electrosurgical instruments of the present invention are employed to efficiently form "perfect arteriotomies" in vessel walls through the passage of a radio frequency current between an active, linear, cutting electrode applied to the vessel wall in alignment with the vessel axis and a ground pad contacting the patient's skin or a ground electrode introduced transluminally into the vessel lumen. The RF current cuts tissue at the active cutting electrode, the cutting rate being dependant on current density through the tissue contacted by the active cutting electrode. Rapid, clean edge slits are made through the vessel wall when current density exceeds a threshold that causes the fluid within the cells to turn to steam, creating a sufficient overpressure so as to burst the cell walls. The cells then dry up, desiccate, and carbonize, resulting in localized shrinking and an opening in the tissue.

Current density depends upon the area the active cutting electrode presents to the vessel wall, the series impedance, typically resistance, to current flow between the active and ground pad or ground electrode, and the voltage applied to the series impedance. Current density is inversely proportional to active electrode contact area, so current density increases as active electrode surface area decreases. The current density is typically adjusted by varying the voltage applied to the active electrode since the area of a particular electrosurgical instrument active electrode is fixed and the series impedance cannot always be controlled.

The series impedance is dependent upon several factors including the material and design of the active cutting electrode, the type, thickness and conductivity of tissue and fluid between the active cutting electrode and the ground pad or electrode, the intimacy of contact of the cutting electrode with the tissue to be cut, and the location of the grounding pad or electrode relative to the cutting electrode. RF energy generators used in this type of surgery have a wide range of power output to accommodate a variety of procedures and devices. For example, the RF energy generator can be adjusted to either cut tissue or to merely cauterize previously cut or torn tissue.

The objective in electrosurgical tissue cutting is to heat the cells of the tissue so rapidly that they explode into steam leaving a cavity in the cell matrix. The heat is meant to be dissipated in the steam and not to dry out adjacent cells. When the electrode is moved and fresh tissue is contacted, new cells are exploded, and the incision is made or continued. The electrical current utilized in electrosurgical cutting is in the radio frequency range and operates by jumping across an air gap to the tissue. This is commonly referred to as sparking. An explanation of electrosurgical cutting theory can be found in the FORCE 1 Instruction Manual published by Valleylab, Inc. of Boulder, Colo., and dated Mar. 1, 1986.

In accordance with the present invention, electrosurgical cutting instruments and associated instruments and methods are provided that can be used in any of the above described full exposure surgical procedures or less invasive MIDCAB or percutaneous exposures of the vessels in question, particularly, the above-described CABG procedures on a stopped or beating heart.

Figure 2:
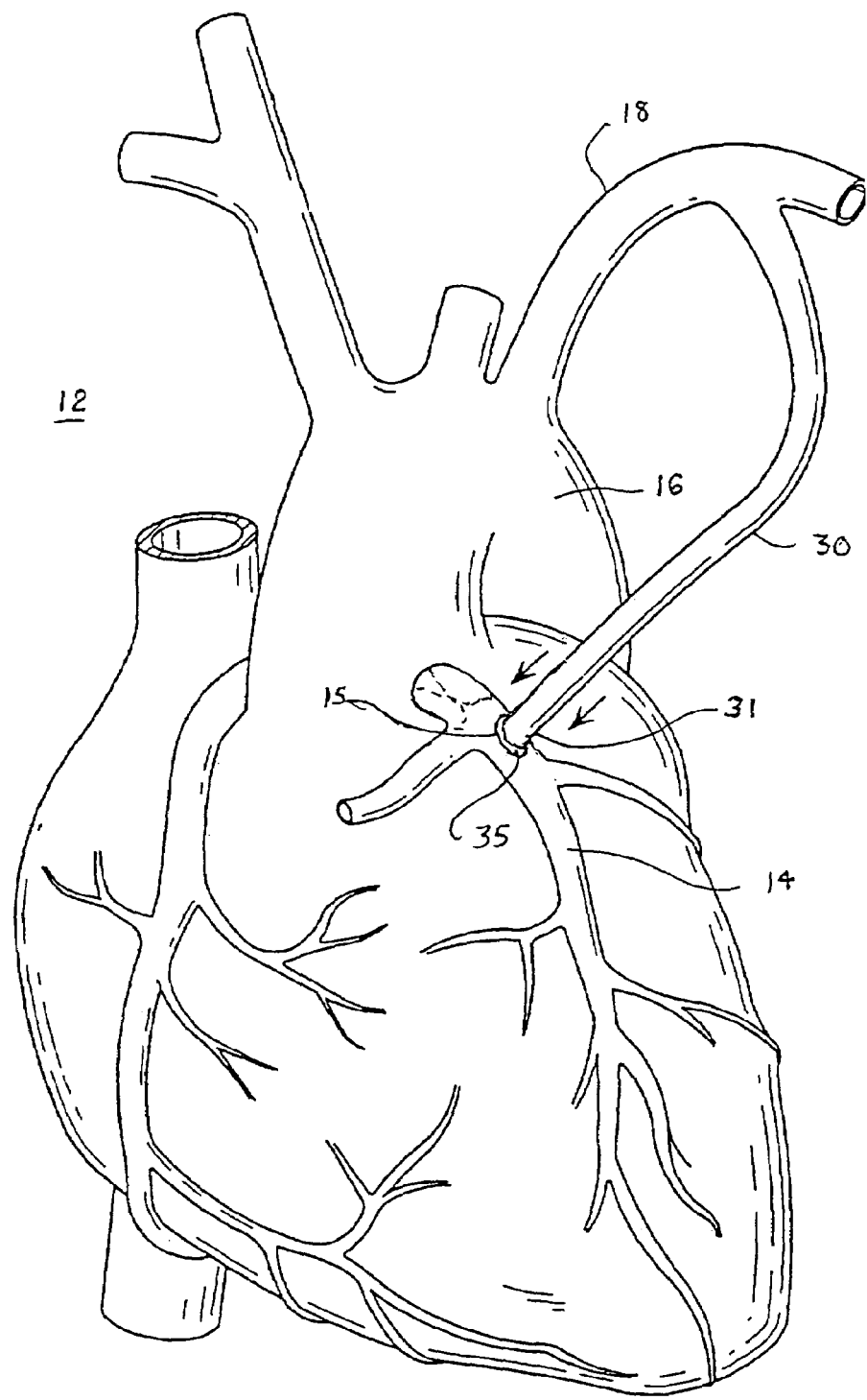
FIG. 2 is a schematic illustration of the end-to-side anastomosis of the source vessel free end to the arteriotomy in the coronary artery.
Figure 4:
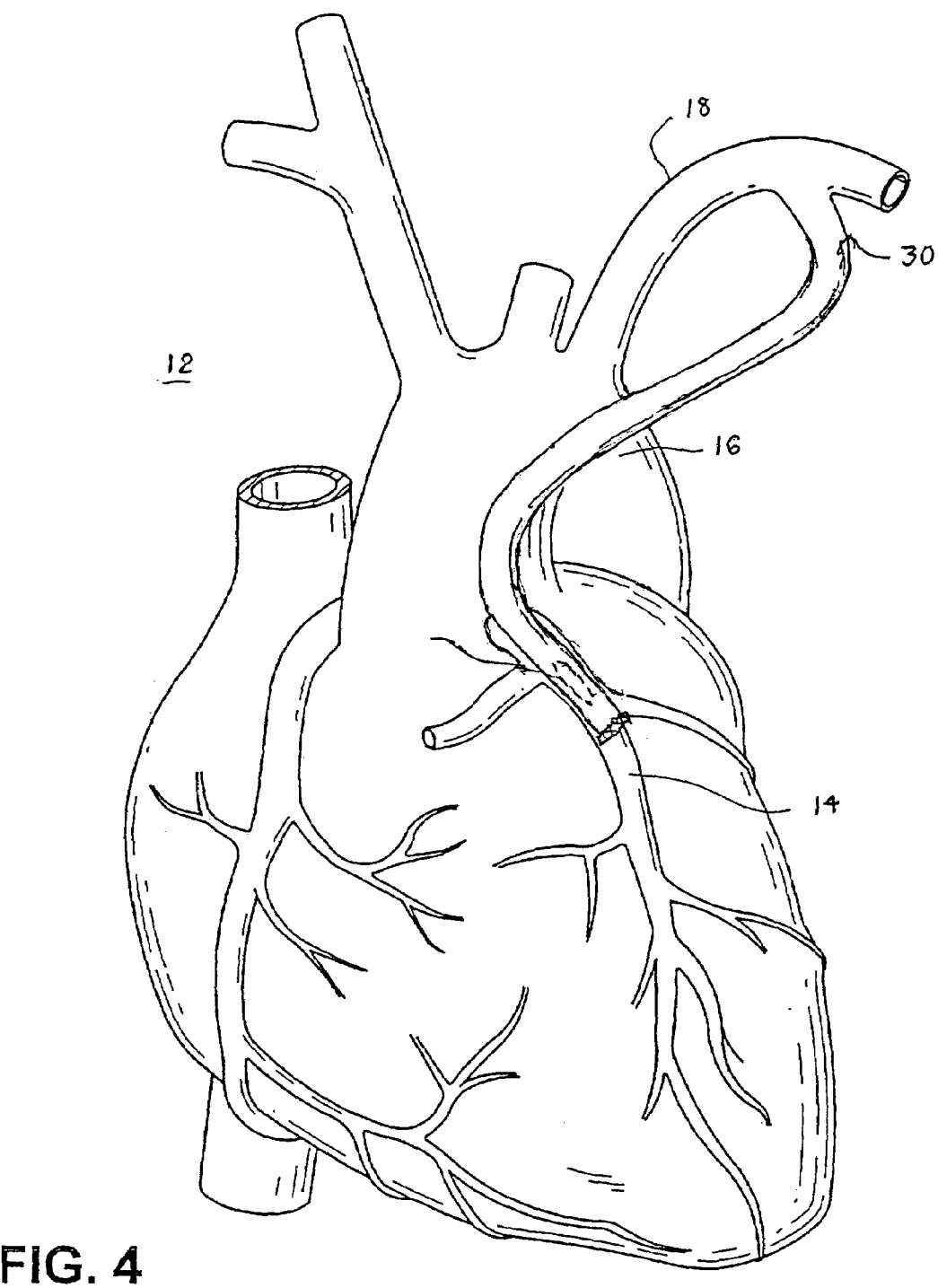
FIG. 4 is a schematic illustration of the side-to-side anastomosis of the arteriotomy in the source vessel to the arteriotomy in the coronary artery.
Figure 5:
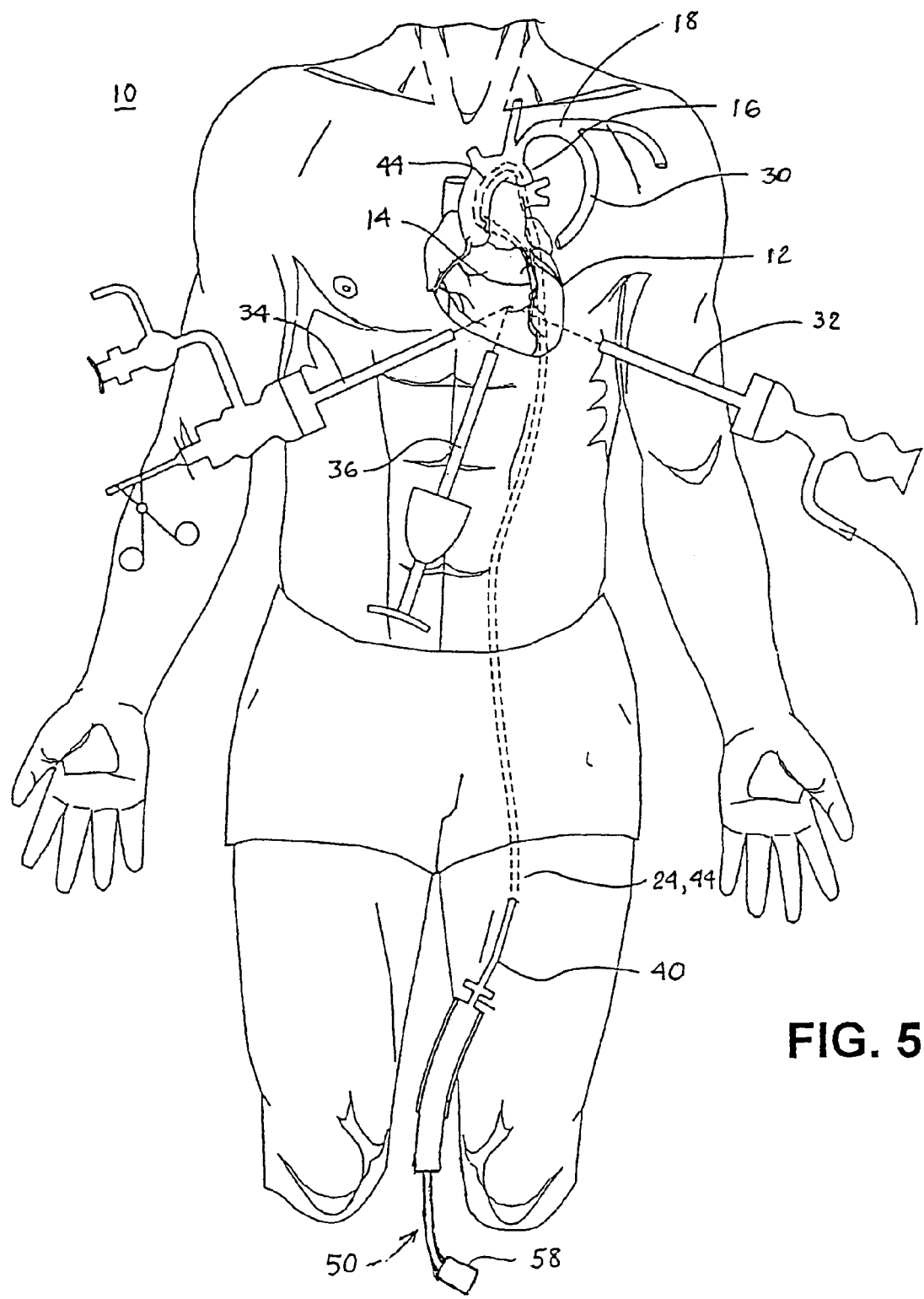
FIG. 5 is an illustration of the preparation of a patient for a percutaneous CABG procedure and particularly the determination of a suitable anastomosis site in a coronary artery.

Exemplary Percutaneous Surgical Exposure:

Thus, for example, FIG. 5 depicts the preparation of the patient 10 for a CABG procedure performed percutaneously and advantageously while the heart 12 is beating. Percutaneous access to the blocked coronary artery and source vessel as well as intra-arterial access into the arterial lumens to effect an artery-to-artery CABG procedure are depicted in FIG. 5. Electrosurgical instruments and methods of the present invention are employed to make the arteriotomy 15 in the side-wall of the LAD coronary artery 14 distal to the site of an obstruction 38 for either of the end-to-side vascular anastomosis as depicted, for example, in FIGS. 1 and 2 or the side-to-side vascular anastomosis as depicted, for example, in FIGS. 3 and 4 and, in the latter procedure, the arteriotomy 33 in the side wall of the freed end portion of the left IMA 30.

It will be understood that an angiography of the coronary arteries of the heart of the patient 10 has been completed to identify the obstruction 38 in the LAD coronary artery 14.

Typically, the surgeon will already have an angiogram of the affected coronary artery available as a result of the earlier diagnosis of the necessity for the coronary bypass.

The patient 10 is placed under general anesthesia, and the patient's left lung is deflated using conventional techniques. The patient 10 is placed in a lateral decubitus position on his right side, and multiple small percutaneous incisions are to be made in the chest wall for the receipt of surgical instruments. As used herein, the term "percutaneous" refers to any penetration through the skin of the patient, whether in the form of a small cut, incision, hole, cannula, trocar sleeve or port or the like. For example, two small incisions are made in the chest wall of patient 10 at different interstitial positions between the patient's ribs, while a third incision is made just below the sternum.

First, the surgeon identifies a suitable position for insertion of a Beress insufflation needle or other suitable needle based upon the pathology and anatomy of the patient 10. Typically, this needle will be inserted between the fifth or sixth intercostal space along the anterior axillary line and into the region between the parietal pleura and the pericardium. The parietal pleura and pericardium are then separated, and the Beress needle is removed.

A first trocar (not shown) having a sharpened tip is inserted in the lumen of port 32 having a diameter of approximately 8 to 12 mm and, preferably, 10 mm, and the assembly is then inserted into the thoracic cavity along the same path traveled by the Beress insufflation needle. The trocar is then removed from port 32 and a conventional endoscopic telescope or thoracoscope (not shown) is introduced through the port 32 into the thoracic cavity. This thoracoscope is used to directly visualize the thoracic cavity and obtain a left lateral view of the pericardial sac or pericardium over the heart 12.

The surgeon determines the best locations for insertion of the assembly of a second trocar (not shown) and port 34 and the assembly of a third trocar (not shown) and port 36 based upon direct visualization through the thoracoscope of the pericardium overlying the heart 12, the presumed locations of the coronary artery of interest and the source artery as well as the anatomy and pathology of the patient 10 may be determined through biplane fluoroscopy and an angiogram. Typically, the second trocar and port 34 is inserted through the intercostal wall and into the thoracic cavity, and the third trocar and port 36 is inserted through the subxyphoid space. Additional trocars or other instruments can be inserted percutaneously as necessary. Often, it will be advantageous to insert a fourth trocar and port for introducing a clipping or suturing device into the thoracic cavity. In each case, the trocars are removed leaving the ports in place.

The parietal pleura is dissected and the pericardial sac is opened by instruments introduced through the second port 34 and/or the third port 36 using conventional techniques while visualizing the site through the thoracoscope. The thoracoscope is used to view the LAD coronary artery 14, in this case, to the extent that it can be seen because of overlying fatty tissue, and the location of the source artery, left IMA 30 in this case.

Figure 3:
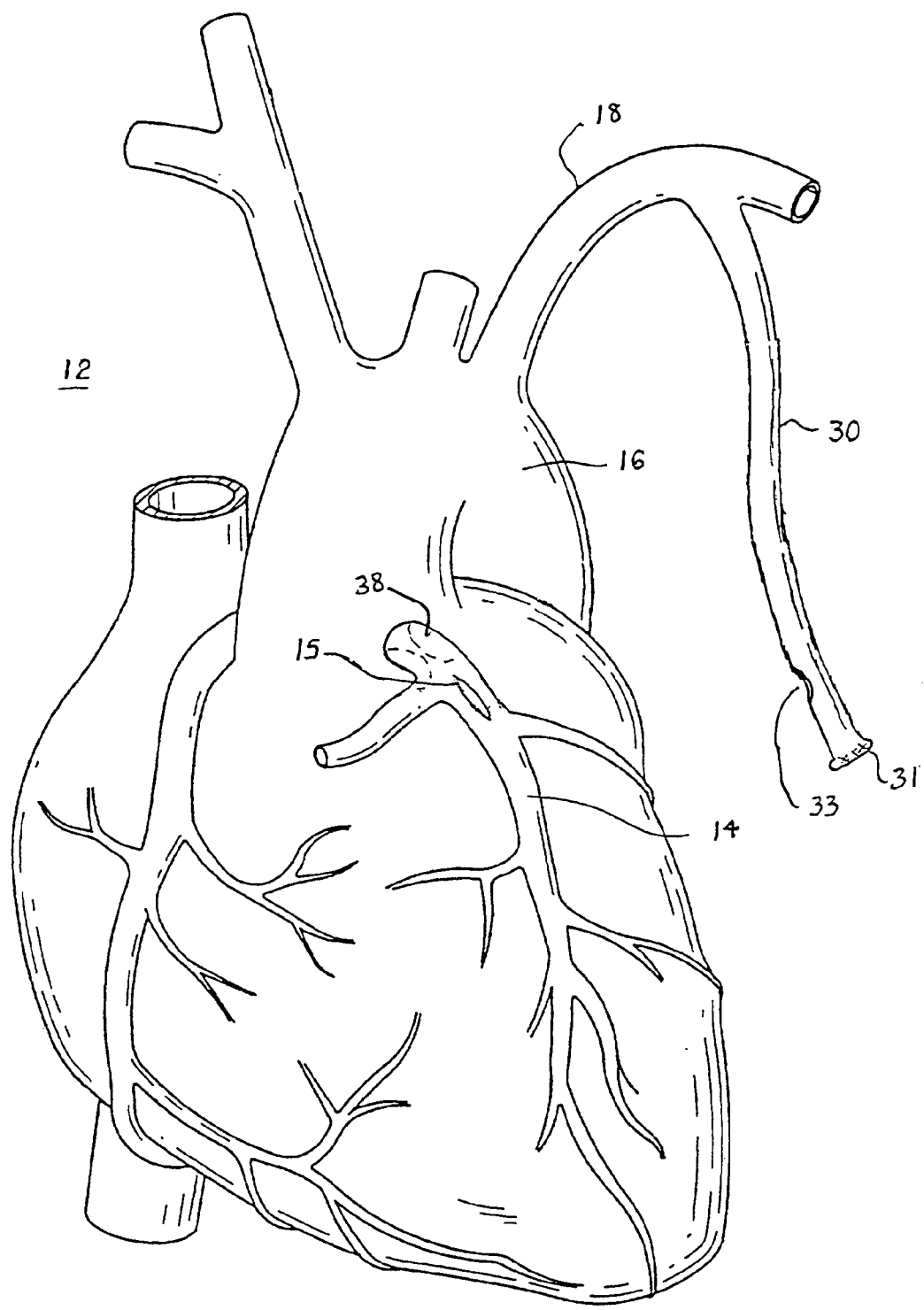
FIG. 3 is a schematic illustration of the preparation of a source vessel free end and an arteriotomy in a coronary artery downstream from an obstruction for a side-to-side anastomosis.

At this juncture, the LAD coronary artery 14 is identified, the location of the occlusion 38 is ascertained, and fatty tissue is dissected away at the proximal and/or distal sites of anastomosis. A distal portion of the left IMA 30 is dissected and freed from tissue as described above. The left IMA distal end 31 is shaped in preparation for the end-to-side anastomosis or the arteriotomy 33 of FIGS. 3 and 4 is performed employing the electrosurgical instruments and methods described in detail herein in preparation for the side-to-side anastomosis.

Figure 6:
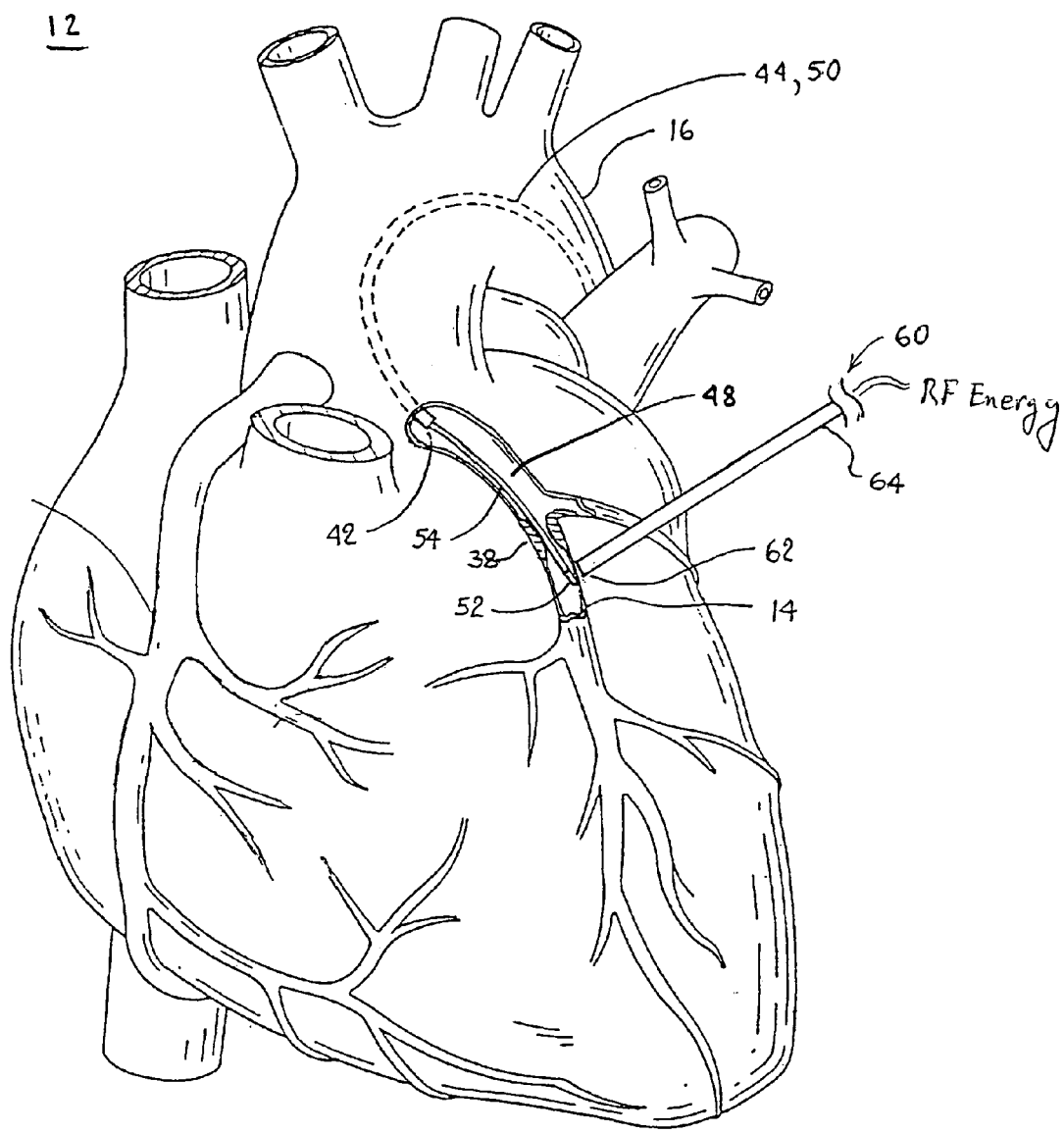
FIG. 6 is a schematic illustration of the application of an electrosurgical cutting electrode to the exterior vessel wall of a coronary artery and a ground electrode within the arterial lumen to form an arteriotomy in the vessel wall.

Electrosurgical Arteriotomy Instruments and Techniques:

In this example of the practice of the present invention, an electrosurgical arteriotomy instrument or tool 60 of one of the types described further herein is inserted through one of the ports 34 or 36 and the opening in the pericardial sac as shown schematically in FIG. 6. The arteriotomy tool distal cutting head 62, having at least one elongated electrosurgical cutting electrode, is directed against the epicardium under visualization employing the thoracoscope extending through port 32. The beating heart 12 is stabilized or stilled in the area surrounding or beside site of the arteriotomy 15 employing one or more of the techniques and devices as described further herein. The axis of the elongated electrosurgical cutting electrode(s) is centered over the exposed arterial vessel wall and aligned to the axis of LAD coronary artery 14 at the arteriotomy site downstream from the obstruction 38. In bipolar embodiments of the arteriotomy tool 60, the return or ground electrode(s) is supported at the arteriotomy tool distal cutting head 62. In unipolar embodiments of the arteriotomy tool 60, a return or ground pad can be applied to the patient's skin. Alternatively, a return or ground electrode is introduced into the lumen of the LAD coronary artery 14 into close proximity with the cutting electrode at the arteriotomy tool distal cutting head 62. RF energy is then applied through the elongated electrosurgical cutting electrode(s) and the return or ground electrode.

Thus, in certain embodiments of the present invention, the catheter body 44 of a femoral catheter 40 is introduced into the femoral artery 24 and advanced into the aorta 16 to locate the femoral catheter distal end 42 at or within the ostium of the LAD coronary artery 14 as shown in FIGS. 5 and 6. An elongated arterial ground wire 50 having a distal ground electrode 52 at or adjacent to the elongated ground wire distal end of the electrically insulated wire body 54 is advanced through the catheter lumen and out of the catheter lumen distal end opening into the lumen 48 of LAD coronary artery 14. The distal ground electrode 52 is then advanced, if possible, through the occlusion 38 to position the distal ground electrode 52 downstream from the occlusion 38 by rotation and back and forth manipulation of the ground wire proximal end 58 exiting the femoral catheter 40 outside the patient's body. A radiopaque ring or the like is carried on the ground wire body 54 at or somewhat proximal to the distal ground electrode 52 so that advancement of the distal ground electrode 52 from the catheter lumen end opening and within the arterial lumen 48 of the LAD coronary artery 14 can be monitored via fluoroscopy.

The progress of the distal ground electrode 52 as it is advanced through or is blocked by the occlusion 38 can also be ascertained employing the electrosurgical tool 60 that is advanced through one of the ports 34 and 36 as a location determining probe. The arteriotomy tool distal cutting head 62 is applied against the epicardium over the suspected location of the LAD coronary artery 14 while the arteriotomy tool distal cutting head 62 and the epicardial surface are observed through the thoracoscope inserted through port 32. The arteriotomy tool distal cutting head 62 is moved about against the epicardium over the suspected location of the LAD coronary artery 14 while low energy electrical current flows through the series impedance between the cutting electrode at the arteriotomy tool distal cutting head 62 and the ground electrode 52. The impedance between the cutting electrode at the arteriotomy tool distal cutting head 62 and the ground electrode 52 can be measured to determine when the cutting electrode at the arteriotomy tool distal cutting head 62 is closest to the ground electrode 52.

The RF energy is applied between the cutting electrode at the arteriotomy tool distal cutting head 62 and the ground electrode 52 within arterial lumen 48 to cut through the wall of the LAD coronary artery 14 after it is determined that the relative locations of the cutting electrode at the arteriotomy tool distal cutting head 62 and the ground electrode 52 are optimized. The elongated electrosurgical cutting electrode is aligned with the axis of and centered over the exposed exterior wall of LAD coronary artery 14, and the applied energy heats and explodes the tissue cells contacted by the elongated cutting element thereby cutting a narrow, straight, clean slit through the arterial wall. The length, width and shape of the slit depends upon the corresponding length, width and shape of the active cutting element at the arteriotomy tool distal cutting head 62.

The impedance of the series circuit between the elongated electrosurgical cutting electrode at the arteriotomy tool distal cutting head 62 and the ground electrode 52 can be monitored during application of the RF energy. The sudden lowered impedance characteristic of passage of the elongated electrosurgical cutting electrode through the vessel wall can be detected and employed to signal completion and/or to automatically terminate the RF energy. The RF energy is automatically cut-off if the cutting electrode at the arteriotomy tool distal cutting head 62 and the ground electrode 52 come into contact.

Overheating of adjacent tissue with accompanying desiccation and damage is advantageously limited or prevented through the particular designs of the electrosurgical cutting instruments or tools 60 of the present invention. Thus, this procedure provides a clean cut at arteriotomy 15 without damage to adjacent tissue. A clean, controlled cut of a prescribed length in axial alignment with the vessel axis and is particularly desirable to assure that tearing does not occur in a direction away from the desired orientation of the cut.

It will be understood that this procedure of forming the arteriotomy 15 can be conducted while the patient's heart 12 is beating or is stopped in the conventional manner. In the former case, miniaturized instruments described herein can be advanced through one of the ports 32, 34, 36 into operative relation with heart 12 for stabilizing a region of the beating heart about the site of the arteriotomy 15 to facilitate its formation and the anastomosis with the source vessel.

A number of electrosurgical cutting instruments or tools 60 are described herein. A first preferred embodiment of a unipolar electrosurgical vessel wall cutting tool 160 is depicted in FIGS. 7–10. The unipolar (i.e., single electrode) electrosurgical vessel wall cutting tool 160 has an elongated tool body 164 extending between the arteriotomy tool distal cutting head 162 and a proximal connector pin 166 that is suitably long enough to be extended through a port 34 or 36 or incision to apply the arteriotomy tool distal cutting head 162 in operative relation to the selected arteriotomy site. The arteriotomy tool distal cutting head 162 comprises a stop ring 170 that provides a frame surrounding an elongated electrosurgical cutting electrode 172 that can be applied against the outer surface of a vessel or arterial wall. The stop ring 170 also stops advancement of the elongated electrosurgical cutting electrode 172 supported within the frame opening into the vessel so as to lessen the likelihood that elongated electrosurgical cutting electrode 172 would be pressed all the way through the vessel lumen and against the opposite side wall of the vessel.

Elongated wire, cutting electrode 172 is supported within the open frame by a pair of electrode support legs 184 and 186 that are electrically connected together and to the distal end of a conductor 168 extending through the tool body 164 to the proximal connector pin 166. The stop ring 170 is formed with an integral proximal ball 190 (partially shown in FIG. 8) that fits within a socket within socket housing 182. The tool body 164 comprises an insulating tube 178 that surrounds the conductor 168. The connector pin 166 receives and is crimped or welded over a proximal end portion of the conductor 168. A heat shrink outer sleeve (not shown) extends over the socket housing 182 and the tube 178. The distal end of the conductor 168 is coupled to the distally extending ends of the elongated electrosurgical cutting electrode 172 by way of a crimp tube extending through the center of the ball of the ball and socket mechanism.

The elongated electrosurgical cutting electrode 172 extends parallel to and is separated by a distance, e.g. about +/−0.030 inches (1.0 mm) from the plane defined by the stop ring 170. In other words, the elongated electrosurgical cutting electrode 172 extends parallel to and can be disposed distally from the plane defined by the stop ring 170 as depicted for convenience in FIGS. 7–10 or more proximally to the plane defined by the stop ring 170.

The elongated electrosurgical cutting electrode 172 is nominally oriented at 90° to the axis of the lead body 164. However, in use, the ball can be rotated within the socket in a single plane "E" so as to adjust the angle of the elongated electrosurgical cutting electrode 172 to the axis of the tool body 164 within a predetermined range so that the elongated electrosurgical cutting electrode 172 can be applied evenly against the vessel wall in axial alignment with the vessel, e.g., the LAD coronary artery 14 as shown in FIG. 10. The tolerances of the ball and socket mechanism can be selected to enable the adjustment to be made in situ by simply pressing the stop ring 170 and elongated electrosurgical cutting electrode 172 against the outer surface of the vessel so as to cause the ball to swivel in the socket.

It will be understood that the ball and socket mechanism can be replaced by a malleable junction of the tool body 164 and the stop ring 170 and that the entire tool body 164 can be made to be malleable to enable manual adjustment of the angle of the elongated electrosurgical cutting electrode 172 to the axis of the lead body 164.

The elongated electrosurgical cutting electrode 172 can be a 5 mm×5 mm square loop of tungsten metal, e.g., the Model LLETZ Loop Electrode available from Valleylab, Inc., of Boulder, Colo. It will be understood that the elongated electrosurgical cutting electrode 172 can have an "L-shape" whereby the elongated electrosurgical cutting electrode 172 is supported by only one of the legs 184 or 186.

The tool body 164 and proximal connector pin 166 can be dimensioned to fit into a hand held electrosurgical pen having a hand held switch, e.g., the Model E2100 or E2550DB from Valleylab, Inc., of Boulder, Colo.

It will be understood that the first preferred embodiment electrosurgical vessel wall cutting tool 160 depicted in FIGS. 7–10 can be employed through a small chest incision with or without use of a port in the percutanous procedure depicted in FIG. 5 as well as in any of the other more invasive surgical procedures to access heart 12 described above and wherein the heart 12 is either stopped or is beating and stabilized as described further herein.

It will also be understood that a ground pad contacting the patient's skin can be substituted for the ground wire 50. Or, one or more elongated electrosurgical cutting electrode and wire ground electrode can be incorporated into the distal cutting heads 62, 162. Therefore, a number of bipolar electrosurgical cutting head examples are depicted in FIGS. 11–19. Certain of the bipolar electrosurgical cutting head examples employ two physically displaced ground electrodes that are electrically connected in common. It will be understood the cutting and wire ground electrodes are spatially separated, usually in axial or parallel alignment, so that they do not come into direct contact but deliver the RF energy through the tissue to be cut in the manner described above. It will also be understood that the designation "elongated electrosurgical cutting electrode" and "wire ground electrode" in the bipolar embodiments is arbitrary and can be reversed in each case.

The tool body in each bipolar electrosurgical vessel wall cutting tool supports a ground conductor extending between the longitudinally extending wire ground electrode(s) and a proximal ground connector element as well as an active conductor extending between the longitudinally extending cutting electrode(s) and a proximal active connector element. The ground and active conductors can be supported in parallel or coaxial alignment and electrically insulated from one another within the tool body. A bifurcated or in-line proximal connector assembly can be employed to support the active and ground connector elements.

A bipolar electrosurgical vessel wall cutting tool 200 is depicted in FIGS. 11 and 12 that is similar to the unipolar electrosurgical vessel wall cutting tool 160 depicted in FIGS. 7–10. The arteriotomy tool distal cutting head 202 comprises an elongated electrosurgical cutting electrode 212 and wire ground electrode 214 supported within and extending from the distal stop ring 210. The active elongated electrosurgical cutting electrode 212 is electrically connected to an active conductor extending through the tool body 204 to the proximal connector pin 208. The wire ground electrode 214 is configured to be similar to the active elongated electrosurgical cutting electrode 212 but is electrically connected to a ground conductor extending through the tool body 204 to the more distal connector ring 206.

The elongated electrosurgical cutting electrode 212 and wire ground electrode 214 are shown in FIGS. 11 and 12 as square loops similar to cutting electrode 172 and support legs 184 and 186, but mounted to distal stop ring 210 to extend outward such that the support legs diverge apart. It will be understood that one of the support legs of each of the elongated electrosurgical cutting electrode 212 and wire ground electrode 214 can be eliminated.

For convenience of illustration, the elongated electrosurgical cutting electrode 212 and wire ground electrode 214 are depicted extending outward from or distal to the plane of stop ring 210 in FIGS. 11 and 12. It will be understood that the elongated electrosurgical cutting electrode 212 and wire ground electrode 214 can be disposed within the stop ring 210 so as to be disposed in a plane or planes proximal to the plane of stop ring 210 in FIGS. 11 and 12.

The arteriotomy tool distal cutting head 202 can be coupled to the tool body 204 by the above-described ball and socket mechanism or can be fixedly attached to the tool body 204. The ball and socket mechanism and the stop ring 210 are eliminated in the latter case.

Figure 15:
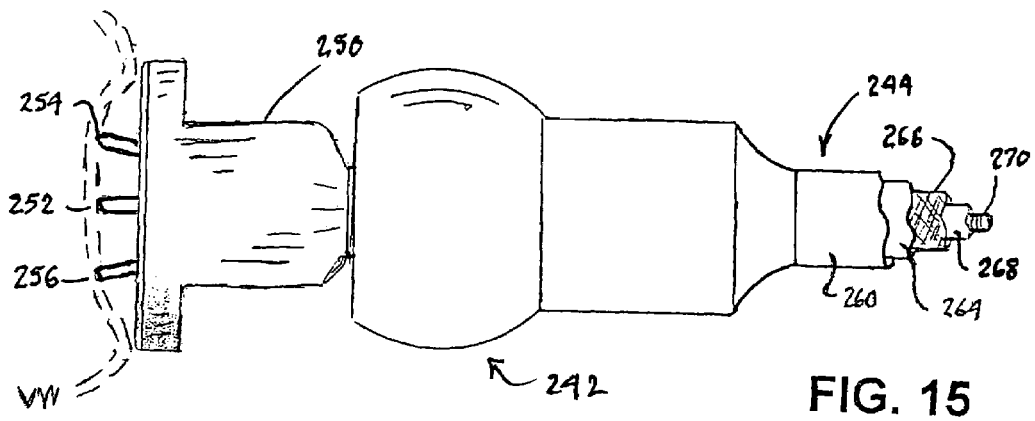
FIG. 15 is an expanded side view of the distal portion of the bipolar electrosurgical vessel wall cutting tool of FIG. 13.
Figure 16:
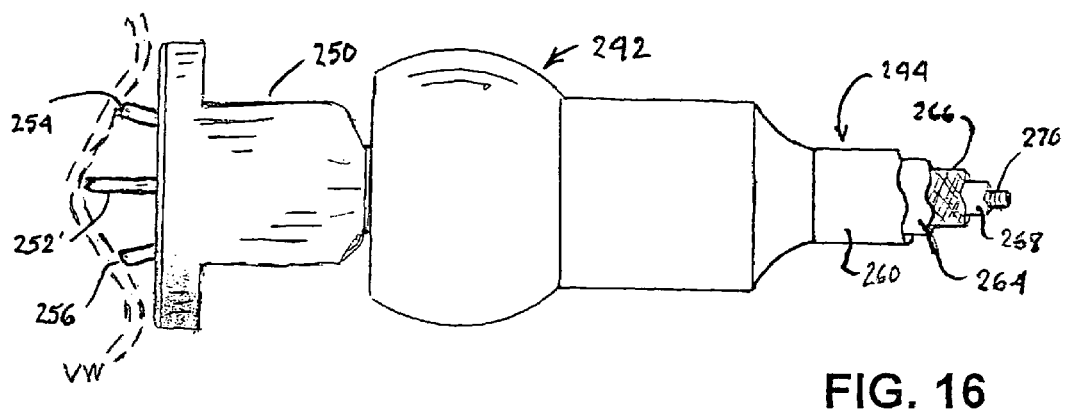
FIG. 16 is an expanded side view of a first variant of the distal portion of the bipolar electrosurgical vessel wall cutting tool of FIG. 13.
Figure 17:
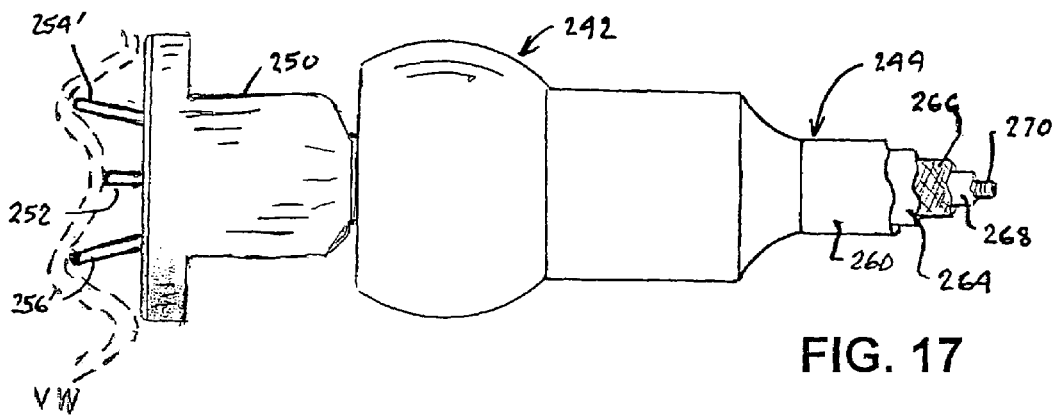
FIG. 17 is an expanded side view of a second variant of the distal portion of the bipolar electrosurgical vessel wall cutting tool of FIG. 13.

Various embodiments of a bipolar electrosurgical vessel wall cutting tool 240 that are similar to the bipolar electrosurgical vessel wall cutting tool 200 are depicted in FIGS. 13–15 and variants are depicted in FIGS. 16 and 17. The arteriotomy tool distal cutting head 242 comprises an elongated electrosurgical cutting electrode 252 and two wire ground electrodes 254 and 256 supported within and extending either within or outward from the distal stop ring 250.

The active elongated electrosurgical cutting electrode 252 is electrically connected to an active conductor 270 extending through the tool body 244 to the proximal connector pin 248. The wire ground electrodes 254 and 256 are configured to be similar to the active elongated electrosurgical cutting electrode 252 but are electrically connected together and to the distal end of a ground conductor 266 that extends through the tool body 244 to the connector ring 246. The conductors 266 and 270 are illustrated as co-axially arranged within insulating 264 and 268 sheaths within the outer sheath 260 of tool body 244 but can be in side-by-side arrangement in separate lumens of tube 264.

The elongated electrosurgical cutting electrode 252 and wire ground electrodes 254 and 256 extend parallel to one another and from the plane defined by the stop ring 250 by a distance, e.g. +/−1.0 mm. The elongated electrosurgical cutting electrode 252 and wire ground electrodes 254 and 256 can be in the same plane as depicted in FIG. 15 or the elongated electrosurgical cutting electrode 252 can be in a different plane that the wire ground electrodes 254 and 256. In a first variation depicted in FIG. 16, the elongated electrosurgical cutting electrode 252' extends further outward from the wire ground electrodes 254 and 256, so that the vessel wall (depicted schematically by the broken line VW is depressed inward more by the elongated electrosurgical cutting electrode 252' than the wire ground electrodes 254 and 256. In a second variation depicted in FIG. 17, the wire ground electrodes 254' and 256' extend further outward from the elongated electrosurgical cutting electrode 252, so that the vessel wall (depicted schematically by the broken line VW is depressed inward more by the wire ground electrodes 254' and 256' than the elongated electrosurgical cutting electrode 252.

The arteriotomy tool distal cutting head 242 can be coupled to the tool body 244 by the above-described ball and socket mechanism or can be fixedly attached to the tool body 244. The fabrication and uses of the bipolar electrosurgical vessel wall cutting tool 240 are similar to those described above with respect to the unipolar electrosurgical vessel wall cutting tool 160.

The elongated electrosurgical cutting electrode 252, 252' and wire ground electrodes 254, '254 and 256, '256 are depicted in FIGS. 13–17 as square loops similar to cutting electrode 172 and support legs 184 and 186, but mounted to distal stop ring 210 to extend such that the support legs of the wire ground electrodes 254, '254 and 256, '256 diverge apart. It will be understood that one of the support legs of each of the elongated electrosurgical cutting electrode 252, 252' and wire ground electrodes 254, '254 and 256, '256 can be eliminated.

For convenience of illustration, the elongated electrosurgical cutting electrode 252, 252' and wire ground electrodes 254, '254 and 256, '256 are depicted extending outward from or distal to the plane of stop ring 210 in FIGS. 13–17. It will be understood that the elongated electrosurgical cutting electrode 252, 252' and wire ground electrodes 254, '254 and 256, '256 can be disposed within the stop ring 210 so as to be disposed in a plane or planes proximal to the plane of stop ring 210 in FIGS. 13–17.

Figure 18:
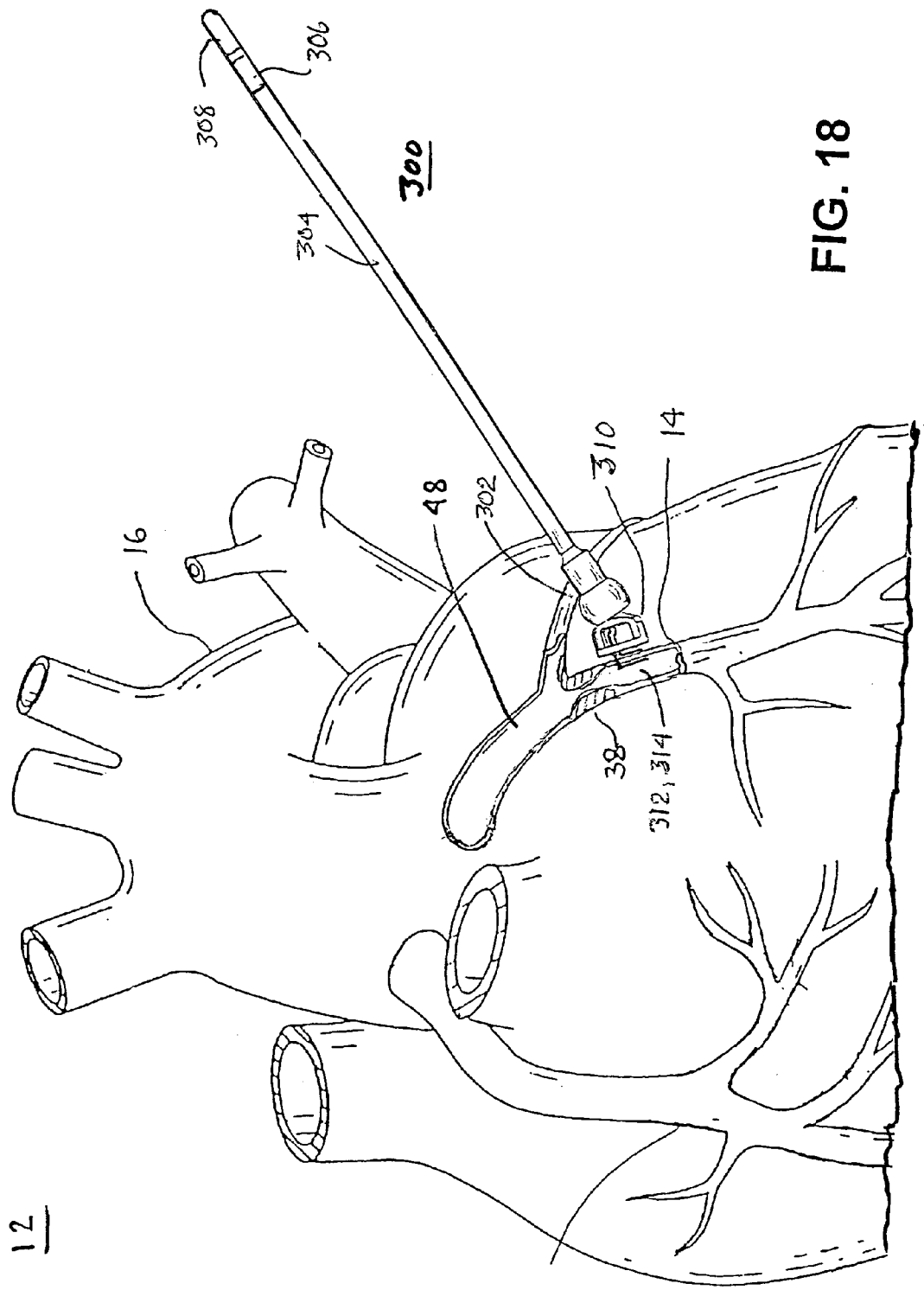
FIG. 18 is a schematic illustration of the application of the electrosurgical instrument wire cutting and ground electrodes of a further embodiment of a bipolar electrosurgical vessel wall cutting tool on either side of the vessel wall of a coronary artery to create an arteriotomy.

A further bipolar electrosurgical vessel wall cutting tool 300 is depicted in FIGS. 18 and 19 and a variant of the electrode configuration is depicted in FIG. 20. In this embodiment, the elongated wire, cutting and ground electrodes 312 and 314 are suspended substantially parallel to one another and in a plane that is not transverse to the tool axis but is substantially aligned with the tool axis. The outermost one of the elongated wire, cutting and ground electrodes 312 and 314 has a sharpened free end 318 that is adapted to be inserted through the vessel wall VW into the vessel lumen. The other of the wire, cutting and ground electrodes 312, 314 is applied against the outer wall of the blood vessel so that the RF energy applied between the wire, cutting and ground electrodes 312, 314, cuts through the vessel wall VW. The wire, cutting and ground electrodes 312, 314 can be pushed through the vessel wall VW or pulled out through the VW as the RF energy is applied as shown by the arrows in FIGS. 19 and 20.

Thus, FIG. 18 depicts the electrosurgical vessel wall cutting tool 300 in use in making an arteriotomy of the LAD coronary artery 14 downstream from the obstruction 38, and FIGS. 19 and 20 depict alternate configurations of the elongated wire, cutting and ground electrodes 312, 314 extending in parallel from the plane of the stop ring 310. For convenience the cutting electrode is.designated as the outermost supported wire electrode having the sharpened tip 318 adapted to penetrate the arterial wall of the LAD coronary artery 14 in the example of use depicted in FIG. 18. Alternatively or in addition to the sharpened tip, RF energy may be used to pass electrode 312 through the vessel wall.

The elongated electrosurgical cutting electrode 312 is electrically connected to an active conductor extending through the tool body 304 to the proximal connector pin 308. The wire ground electrode 314 is configured to be similar to the active elongated electrosurgical cutting electrode 312 but is electrically connected to a ground conductor extending through the tool body 304 to the more distal connector ring 306. The elongated electrosurgical cutting electrode 312 and wire ground electrode 314 extend parallel to and are separated apart by a distance that approximates the average vessel wall VW thickness and from the plane defined by the stop ring 310 by a distance, e.g. 1.0 mm.

Alternatively, electrosurgical vessel wall cutting tool 300 may be configured as a monopolar device (not shown) comprising the elongated cutting electrode 312. In this embodiment, RF energy is applied through the elongated cutting electrode 312 and to a remote grounding pad. The elongated cutting electrode 312 may have a sharpened free end 318 that is adapted to be inserted through the vessel wall VW into the vessel lumen and/or RF energy may be used to help pass electrode 312 through the vessel wall. Once the cutting electrode 312 is within the vessel lumen, electrode 312 is pulled out through the VW while RF energy is applied, thereby forming the arteriotomy.

Figure 21:
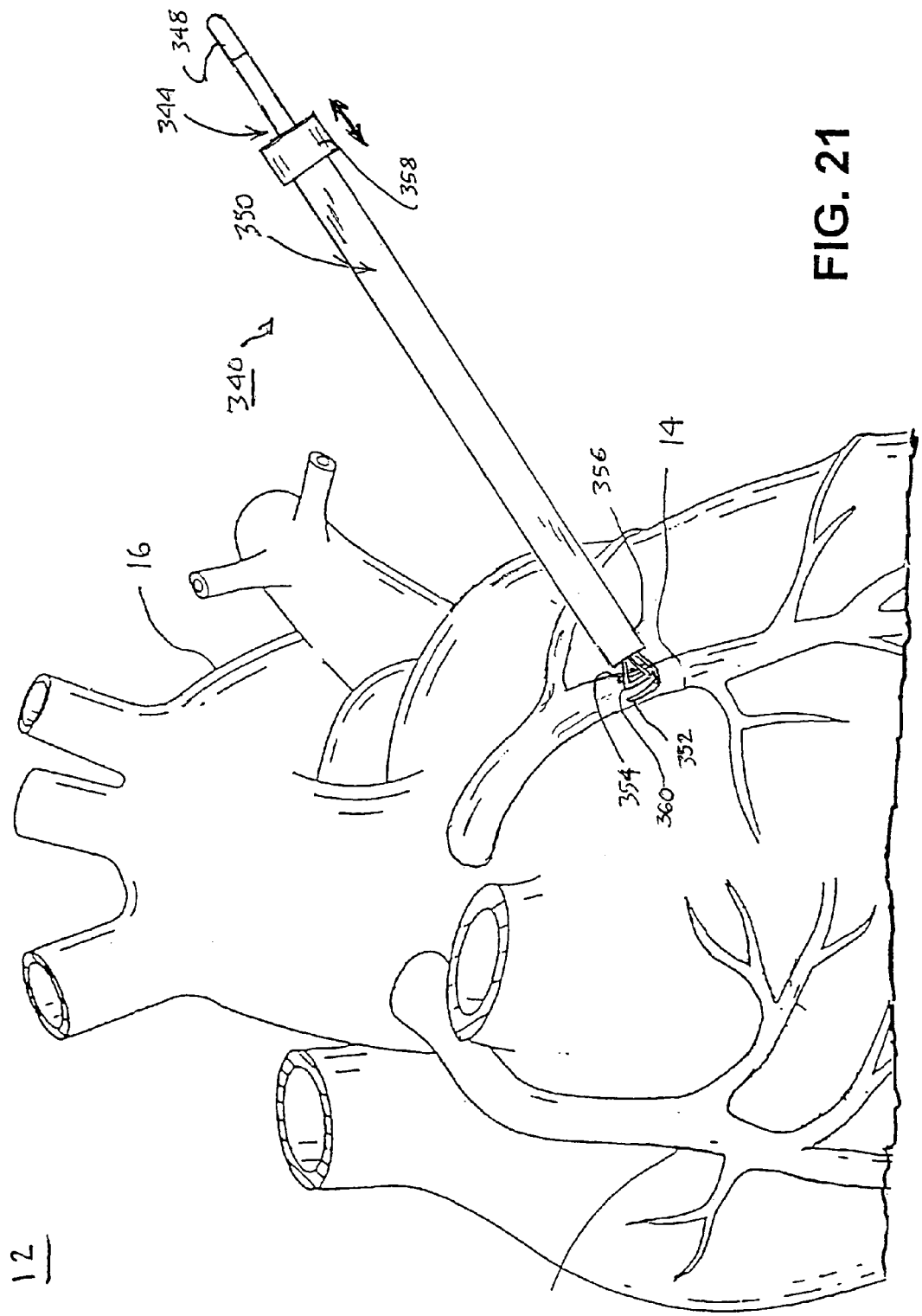
FIG. 21 is a schematic illustration of the application of the electrosurgical instrument wire cutting and ground electrodes of a still further embodiment of a bipolar electrosurgical vessel wall cutting tool to the outer surface of the vessel wall of a coronary artery to create an arteriotomy.
Figure 22:
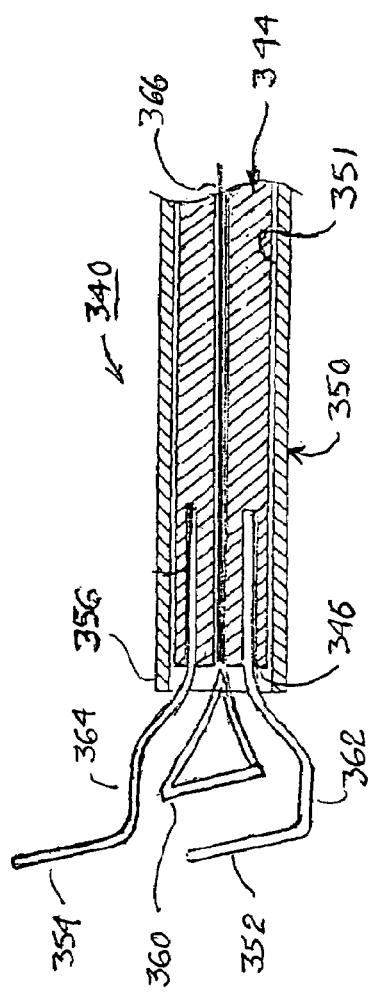
FIG. 22 is an expanded side view of the distal portion of the bipolar electrosurgical vessel wall cutting tool of FIG. 21 with the wire cutting and ground electrodes separated apart in a non-operative configuration.
Figure 23:
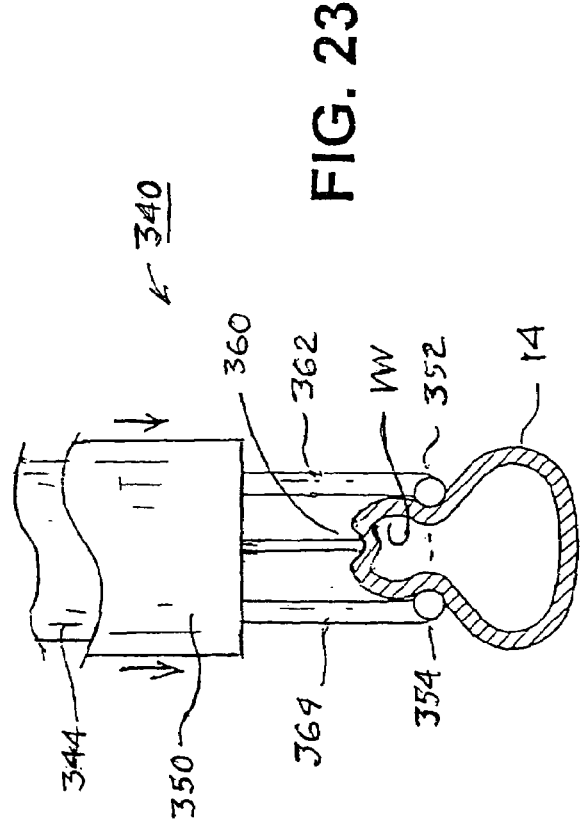
FIG. 23 is an expanded side view of the distal portion of the bipolar electrosurgical vessel wall cutting tool of FIG. 21 with the wire cutting and ground electrodes drawn together engaging a portion of the vessel wall to create an arteriotomy.

A still further unipolar electrosurgical vessel wall cutting tool 340 is depicted in FIGS. 21–23 and comprises an outer sleeve 350 and a tool body 344 fitted within the outer sleeve lumen 351. The outer sleeve 350 extends between a distal sleeve end 356 and a proximal sleeve knob 358. The tool body 344 supports an elongated electrosurgical cutting electrode 360 extending away from the tool body distal end 346. The cutting electrode 360 is electrically connected to the distal end of an active conductor 366 extending through the tool body 344 to a proximal connector pin 348. A pair of grasping pincers 352 and 354 are supported by pincer legs 364 and 366, respectively, that extend through tool body distal end 345 and into the tool body 344. The pincer legs 362 and 364 have a preformed shape that extends the elongated grasping pincers 352 and 354 to extend substantially parallel to one another and to the elongated electrosurgical cutting electrode 360.

The elongated grasping pincers 352 and 354 are thus suspended substantially parallel to one another and in a plane that is substantially transverse to the tool axis. The distance between the elongated grasping pincers 352 and 354 can be drawn together from the distance depicted in FIG. 22 to the distance depicted in FIG. 23 by advancing the sleeve 350 over the pincer legs 362 and 364. The grasping pincers 352 can therefore be used to engage and compress a portion of the vessel wall VW together as depicted in FIG. 23.

Thus, FIG. 21 depicts the electrosurgical vessel wall cutting tool 340 in use in making an arteriotomy of the LAD coronary artery 14 downstream from the obstruction 38, and FIGS. 22 and 23 depict how the distance between the elongated grasping pincers 352 and 354 can be adjusted by remote manipulation of the cutting tool 340. In one preferred procedure, the electrosurgical vessel wall cutting tool 340 is advanced in the configuration shown in FIG. 22 through a port or incision to press the elongated electrosurgical cutting electrode 360 in axial alignment with the vessel axis and against the outer surface of the vessel wall VW of the vessel, e.g., LAD coronary artery 14 at the arteriotomy site.

The sleeve 350 and tool body 344 are then manipulated into the configuration shown in FIG. 23 to draw the pincer legs 362 and 364 into the sleeve lumen 351 and compress a portion of the vessel wall VW between the elongated wire grasping pincers 352 and 354. The elongated electrosurgical cutting electrode 360 makes intimate contact with the vessel wall squeezed together by the elongated grasping pincers 352 and 354. Then, RF energy is applied through an elongated electrosurgical cutting electrode 360 and to a remote grounding pad or a wire ground electrode, e.g., ground wire electrode 52 depicted in FIG. 10, disposed within the lumen of the vessel, e.g., LAD coronary artery 14. Alternatively, grasping pincers 352 and/or 354 may be grounding electrodes.

Stabilization:

All of the above-described electrosurgical vessel wall cutting tools 60, 160, 200, 240, 300, and 340, and equivalents thereto, can be employed in CABG procedures that are conducted while the heart is either arrested or beating. It may be preferable to employ further heart stabilization tools and techniques to stabilize the heart around the site of the arteriotomy 15 in LAD coronary artery 14 and to minimize blood loss through the arteriotomy. To this end, any of the instruments and techniques for applying pressure against the epicardial surface can be employed, e.g., the instruments mounted to the retractors maintaining the chest wall incision and the techniques disclosed in the above-referenced '782 patent. Or, a frame of the type described in the above-referenced '069 patent can be temporarily sutured to or held against the epicardium to immobilize the area and compress the artery lumen.

Alternatively, suction can be applied to the epicardial surface as shown for example in the above-referenced '295 patent or in commonly assigned U.S. Pat. No. 6,394,948 and PCT Publication WO 02/28287 wherein the instruments and suction elements are mounted to the surgical table or another stable platform. The Octopus® flexible tissue stabilization system sold by assignee of the present application can be employed to grip and stabilize or immobilize the epicardial surface tissue on either side of the site of a vessel wall where an elongated slit is to be made.

Figure 24:
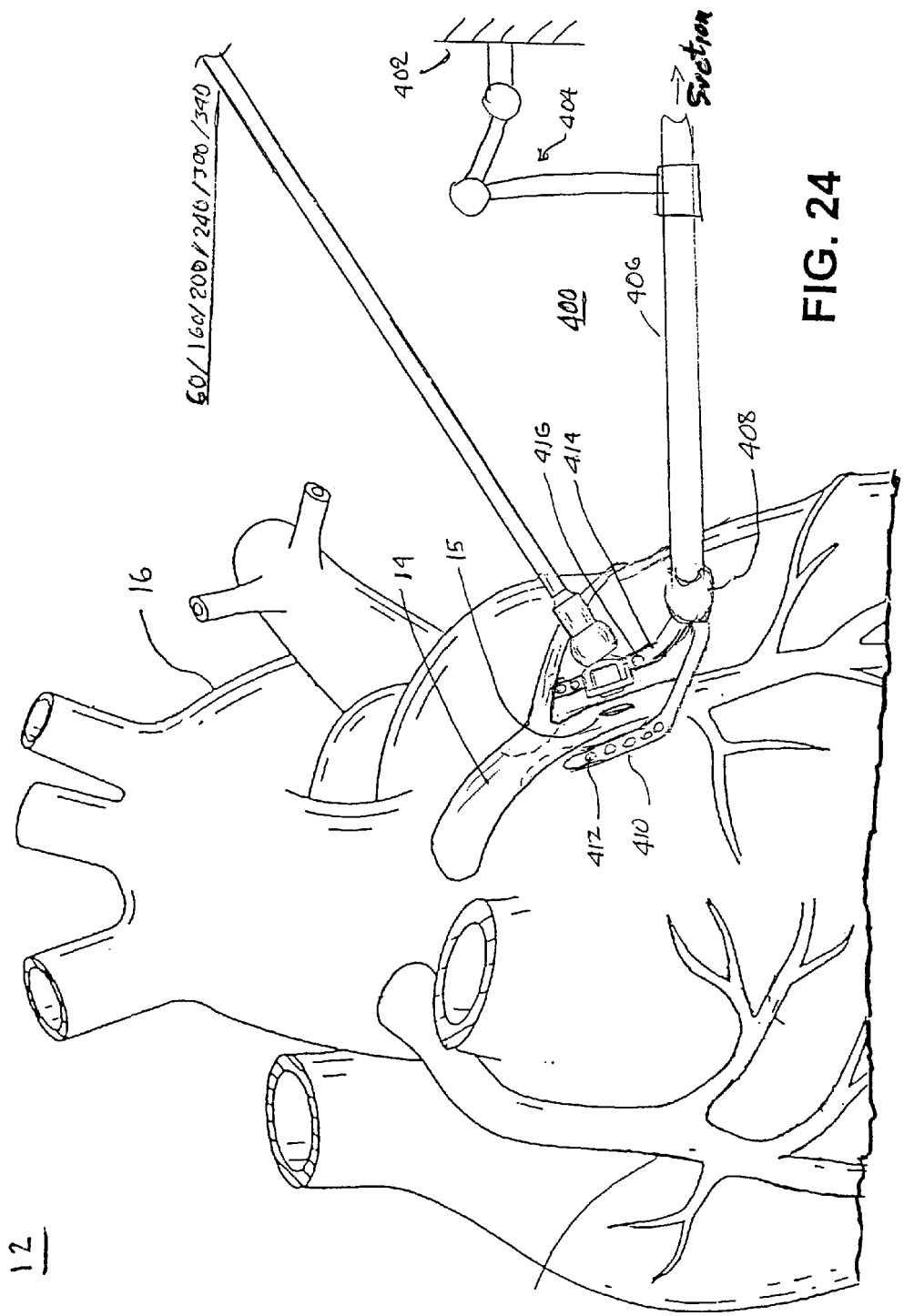
FIG. 24 is a schematic illustration of the application of a further embodiment of an electrosurgical vessel wall cutting tool of the invention applied to the outer surface of the wall of a coronary artery to create an arteriotomy as an area of the beating heart is immobilized by suction.

Thus, the use of such a tissue stabilization system 400 to stabilize or immobilize the epicardial surface tissue on either side of the site of the arteriotomy 15 in LAD coronary artery 14 is illustrated schematically in FIG. 24. An articulating or flexible arm 404, 406, is attached to a fixed reference 402, which can be a retractor affixed to an opening in the patient's chest wall or other operating room equipment, e.g., an operating table. A vacuum source is coupled to a lumen of the arm 406 or to flexible tubing (not shown) that in either case extends into the interior manifolds of stabilizer suction pads 410 and 414 that extend on either side of the site of the arteriotomy 15. In this example, the stabilizer suction pads 410 and 414 are formed as described in the above-referenced PCT Publication WO 02/28287, for example. A plurality of suction ports 412 and 416 extend through surfaces of the suction pads 410 and 414, respectively that are applied against the epicardial surface from manifolds within the suction pads 410 and 414. In this illustrated embodiment, the manifolds within the suction pads 410 and 414 are coupled through an air passage within joint 408 to a suction tube or lumen of the arm 406 that extends to a vacuum port (not shown). Instead, flexible tubing could be employed as in the Octopus® flexible tissue stabilization system to apply suction from the vacuum source directly into each of the manifolds within the suction pads 410 and 414. It will be understood that a single horseshoe shaped or rectilinear suction pad could be substituted for the pair of stabilizer suction pads 410 and 414.

In use, the stabilizer suction pads 410 and 414 are lined up with the axis of the LAD coronary artery 14 (or other target vessel). The vacuum source creates suction between the epicardium and the suction pads 410 and 414 to minimize heart movement in the area around the site of the arteriotomy. The stabilizer suction pads 410 and 414 can be spread apart in the manner of the Octopus® flexible tissue stabilization system to further immobilize the tissue area around the site of the arteriotomy 15.

The ground electrode and elongated electrosurgical cutting electrode of the above-described electrosurgical vessel wall cutting tools 60, 160, 200, 240, 300, and 340, and equivalents thereto can be applied to the site. RF energy is then applied between the elongated electrosurgical cutting electrode and the ground electrode in the interval between heart contractions.

It is also contemplated that the above-described electrosurgical tools incorporate immobilization devices, e.g., pressure applying feet alongside or frames surrounding the arteriotomy tool distal cutting head. Any of the above-described electrosurgical tools 60 can be modified to incorporate such pressure applying feet or frames.

Figure 25:
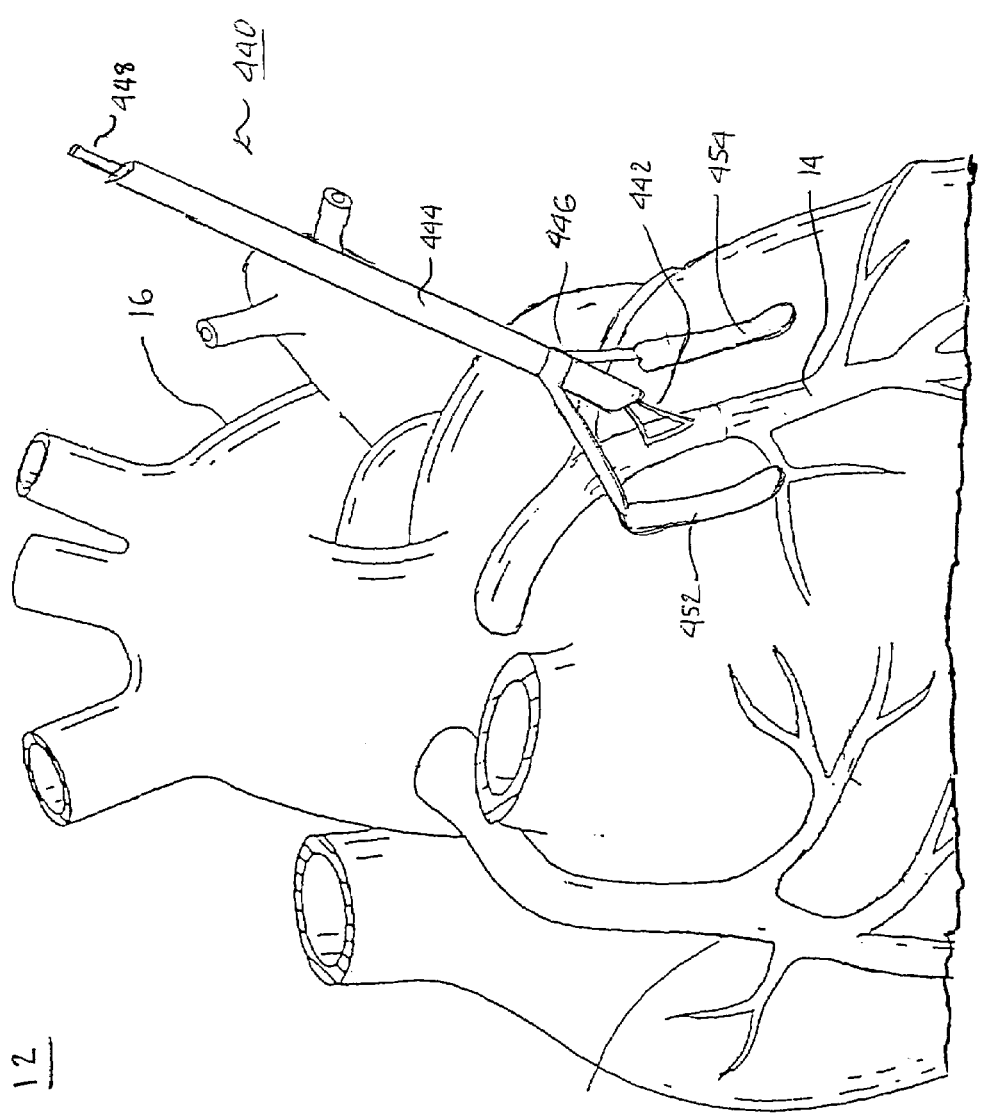
FIG. 25 is a schematic illustration of the application of a further embodiment of an electrosurgical vessel wall cutting tool of the invention applied to the outer surface of the wall of a coronary artery to create an arteriotomy as an area of the beating heart is immobilized by pads extending from the electrosurgical vessel wall cutting tool alongside the artery.

For example, FIG. 25 depicts a bipolar or unipolar electrosurgical vessel wall cutting tool 440 in use in making an arteriotomy of the LAD coronary artery 14 having an elongated electrosurgical cutting electrode 442 of any of the above described types with or without a ball and socket mechanism and stop ring. Stabilizer feet 452 and 454 are coupled to the tool body 444 at junction 446. A unipolar electrosurgical vessel wall cutting tool 440 that is adapted to be employed with a remote ground pad on the patient's skin or a ground wire 50 introduced into the vessel lumen such that the ground or return electrode 52 is located in proximity to the cutting electrode as described above with respect to FIG. 6 is illustrated for convenience of description.

The electrosurgical vessel wall cutting tool 440 comprises a tool body 444 extending from an elongated electrosurgical cutting electrode 442 at the tool body distal end to a coupling tool connector element 448 adapted to be coupled to a source of RF energy at the tool body proximal end. The electrosurgical cutting electrode 442 is supported to extend outward or distally and substantially transversely to the axis of the tool body 444. An electrical conductor extends through a conductor lumen of the tool body 444 between the elongated electrosurgical cutting electrode 442 and connector element 448.

For example, the electrosurgical vessel wall cutting tool 440 can be introduced into the chest cavity in any of the above-described surgical access procedures so that the elongated electrosurgical cutting electrode 442 is aligned with the axis of and centered over exposed vessel wall of the LAD coronary artery 14 at the site where an arteriotomy is to be made and stabilizer feet 452 and 454 are brought to bear against the epicardium. The surgeon applies pressure through the tool body 444 to press the stabilizer feet 452 and 454 against the epicardium and to press the elongated electrosurgical cutting electrode 442 against the vessel wall. Heart movement is minimized in the area around the site of the arteriotomy by the applied pressure, and RF energy is applied to the elongated electrosurgical cutting electrode 442 in the interval between heart contractions.

Figure 26:
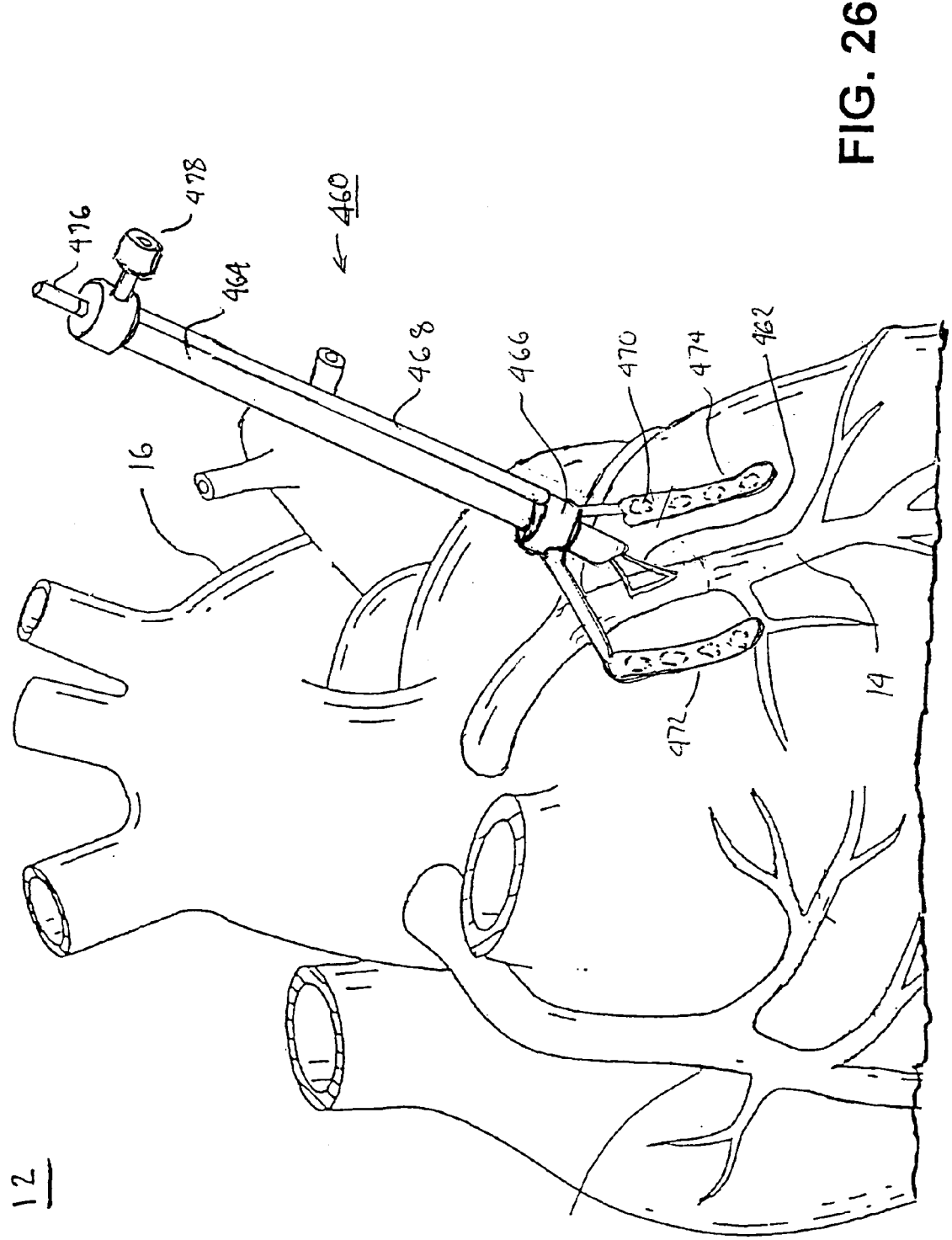
FIG. 26 is a schematic illustration of the application of a further embodiment of an electrosurgical vessel wall cutting tool of the invention applied to the outer surface of the wall of a coronary artery to create an arteriotomy as an area of the beating heart is immobilized by suction pads extending from the electrosurgical vessel wall cutting tool alongside the artery.

FIG. 26 depicts another example of a bipolar or unipolar electrosurgical vessel wall cutting tool 460 in use in making an arteriotomy of the LAD coronary artery 14 having an elongated electrosurgical cutting electrode 462 of any of the above described types with or without a ball and socket mechanism and stop ring. A unipolar electrosurgical vessel wall cutting tool 460 that is adapted to be employed with a remote ground pad on the patient's skin or a ground wire 50 introduced into the vessel lumen such that the ground or return electrode 52 is located in proximity to the cutting electrode as described above with respect to FIG. 6 is illustrated for convenience of description.

The electrosurgical vessel wall cutting tool 460 comprises a tool body 464 extending from an elongated electrosurgical cutting electrode 462 at the tool body distal end to a coupling tool connector element 476 adapted to be coupled to a source of RF energy and a vacuum port 478 adapted to be coupled with a vacuum source at the tool body proximal end. The electrosurgical cutting electrode 462 is supported to extend outward or distally and substantially transversely to the axis of the tool body 464. An electrical conductor extends through a conductor lumen of the tool body 464 between the elongated electrosurgical cutting electrode 462 and connector element 476.

Stabilizer suction pads 472 and 474 are coupled to the tool body 464 at manifold 466 to extend on either side of the elongated electrosurgical cutting electrode 462. In this example, the stabilizer suction pads 472 and 474 are formed as described in the above-referenced PCT Publication WO 02/28287, for example. A plurality of suction ports 470 extend through surfaces of the suction pads 472 and 474 that are applied against the epicardial surface from a manifold or plenum within the suction pads 472 and 474 that is in turn coupled through air passages within manifold 466 to a suction tube or lumen 468 of the tool body 464 that extends to the vacuum port 478.

In use, the stabilizer suction pads 472 and 474 and elongated electrosurgical cutting electrode 462 are lined up with the axis of the LAD coronary artery 14 (or other target vessel). The vacuum source creates suction between the epicardium and the suction pads 472 and 474 to minimize heart movement in the area around the site of the arteriotomy. RF energy is applied to the elongated electrosurgical cutting electrode 462 in the interval between heart contractions.

It will be understood that a single horseshoe shaped or rectilinear suction pad could be substituted for the pair of stabilizer suction pads 472 and 474.

Figure 27:
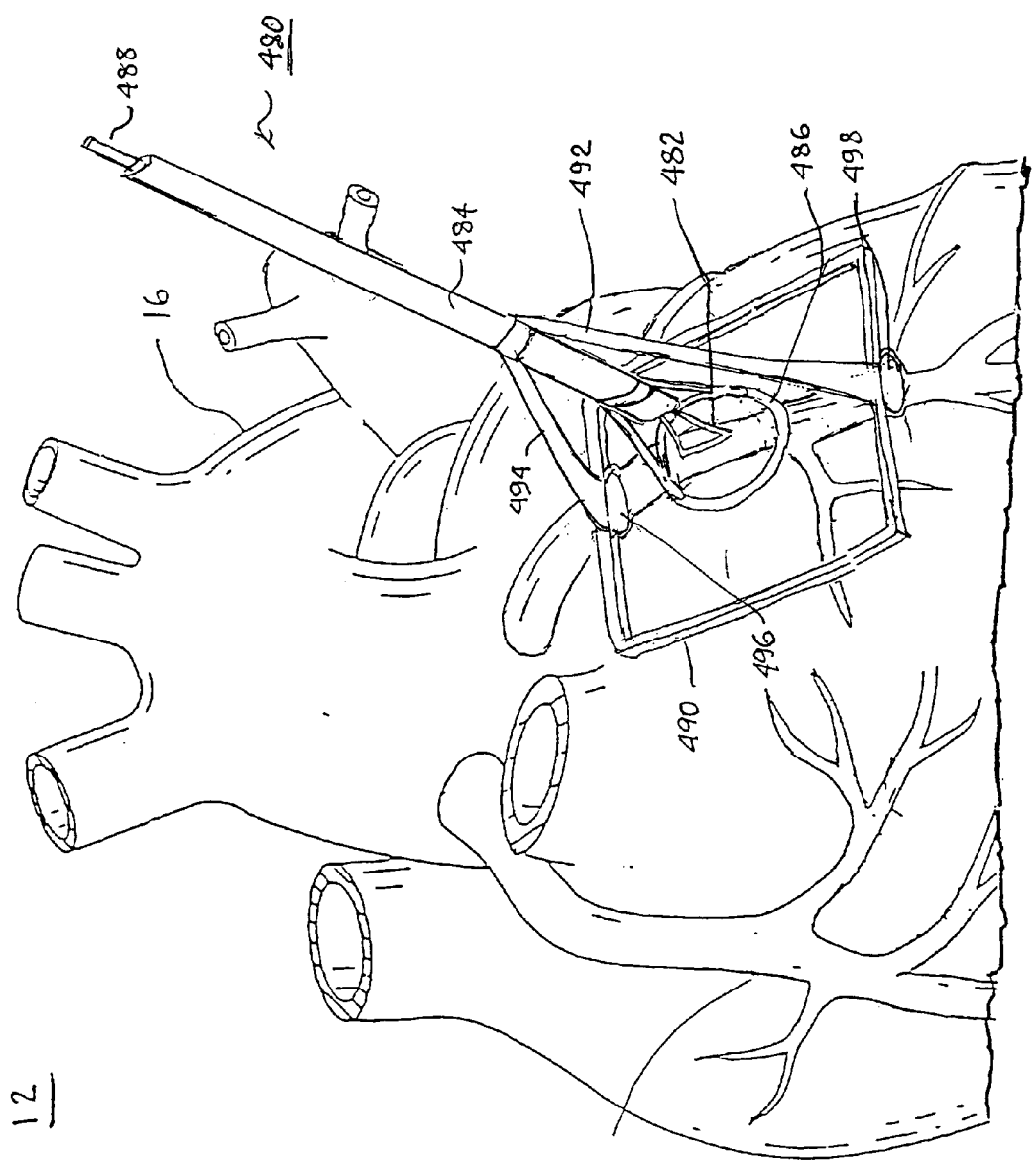
FIG. 27 is a schematic illustration of the application of a further embodiment of an electrosurgical vessel wall cutting tool of the invention applied to the outer surface of the wall of a coronary artery to create an arteriotomy as an area of the beating heart is immobilized and the vessel occluded by a frame extending from the electrosurgical vessel wall cutting tool alongside the artery.

It is also desirable to both stabilize the area of the heart about the arteriotomy site and to occlude the target vessel lumen upstream and downstream of the arteriotomy site. A further bipolar or unipolar electrosurgical vessel wall cutting tool 480 that combines an elongated electrosurgical cutting electrode 482 of any of the above described types with or without a ball and socket mechanism and stop ring with a stabilization and vessel occlusion frame 490 is depicted in FIG. 27 in use in making an arteriotomy of the LAD coronary artery 14. A unipolar electrosurgical vessel wall cutting tool 480 that is adapted to be employed with a remote ground pad on the patient's skin or a ground wire 50 introduced into the vessel lumen such that the ground or return electrode 52 is located in proximity to the cutting electrode as described above with respect to FIG. 6 is illustrated for convenience of description.

The electrosurgical vessel wall cutting tool 480 comprises a tool body 484 extending from an elongated electrosurgical cutting electrode 482 at the tool body distal end to a coupling tool connector element 488 adapted to be coupled to a source of RF energy at the tool body proximal end. The electrosurgical cutting electrode 482 is supported to extend outward or distally and substantially transversely to the axis of the tool body 484. An electrical conductor extends through a conductor lumen of the tool body 484 between the elongated electrosurgical cutting electrode 482 and connector element 488.

In this embodiment, the electrosurgical cutting electrode 482 attached to tool body 484 is surrounded by a stop ring 486. Frame struts 492 and 494 extend from a coupling ring about the tool body 484 to a rectilinear stabilization and vessel occlusion frame 490. Occlusion pads 496 and 498 extend distally from the frame 490.

In use, the elongated electrosurgical cutting electrode 482 is aligned with the axis of the LAD coronary artery 14 (or other target vessel), and the occlusion pads are positioned over the LAD coronary artery. The surgeon applies pressure through the tool body 484 to press frame 490 against the epicardium and to press the elongated electrosurgical cutting electrode 482 against the vessel wall and stop ring 486 against the epicardium. The occlusion pads 496 and 498 extend further than the frame 490 into the vessel walls to occlude the LAD coronary artery 14. Heart movement is thereby minimized in the area around the site of the arteriotomy by the applied pressure, and RF energy is applied to the elongated electrosurgical cutting electrode 482 in the interval between heart contractions.

It will be understood that the features of the electrosurgical tools 460 and 480 can be combined by forming the pair of stabilizer suction pads 472 and 474 in the shape of the rectilinear frame 490 having the occlusion pads 496 and 498 extending distally from the frame 490.

A still further embodiment of a bipolar or unipolar electrosurgical vessel wall cutting tool 500 is depicted in FIGS. 28–32, wherein suction is applied through an arcuate suction pad and lumen of the tool body to draw the vessel wall against the elongated electrosurgical cutting electrode. The suction pad is configured to facilitate the axial alignment of the elongated electrosurgical cutting electrode with the vessel axis and the centering of the elongated electrosurgical cutting electrode over the exposed vessel wall. A unipolar electrosurgical vessel wall cutting tool 500 that is adapted to be employed with a remote ground pad on the patient's skin or a ground wire 50 introduced into the vessel lumen such that the ground or return electrode 52 is located in proximity to the cutting electrode as described above with respect to FIG. 6 is illustrated for convenience of description.

Thus, the electrosurgical vessel wall cutting tool 500 comprises a tool body 502 extending from a suction pad 504 and elongated electrosurgical cutting electrode 510 at the tool body distal end to a coupling tool connector element 506 and a vacuum port 508 adapted to be coupled with a vacuum source at the tool body proximal end. The electrosurgical cutting electrode 510 is supported to extend outward or distally from inner surface 512 of suction pad 504 and to extend substantially transversely to the axis of the tool body 502. An electrical conductor extends through a conductor lumen of the tool body 502 between the elongated electrosurgical cutting electrode 510 and connector element 506.

A plurality of suction ports 516 extend through the suction pad inner surface 512 from a manifold or plenum within the arcuate suction pad 504 that is in turn coupled to a further suction lumen of the tool body 502 that extends to the vacuum port 508. The cutting pad 504 is arcuate in cross-section such that the suction pad inner surface 512 can be fitted over and against an exposed arcuate section of vessel wall that is surgically accessed, and suction can be applied through the suction ports 516 to draw the vessel wall against the suction pad inner surface 512 and elongated electrosurgical cutting electrode 510. For example, the electrosurgical vessel wall cutting tool 500 can be introduced into the chest cavity in any of the above-described surgical access procedures so that the suction pad inner surface 512 and electrosurgical cutting electrode 510 are brought into axial alignment with a portion of a coronary artery, e.g., LAD coronary artery 14, at the site where an arteriotomy is to be made.

Figure 28:
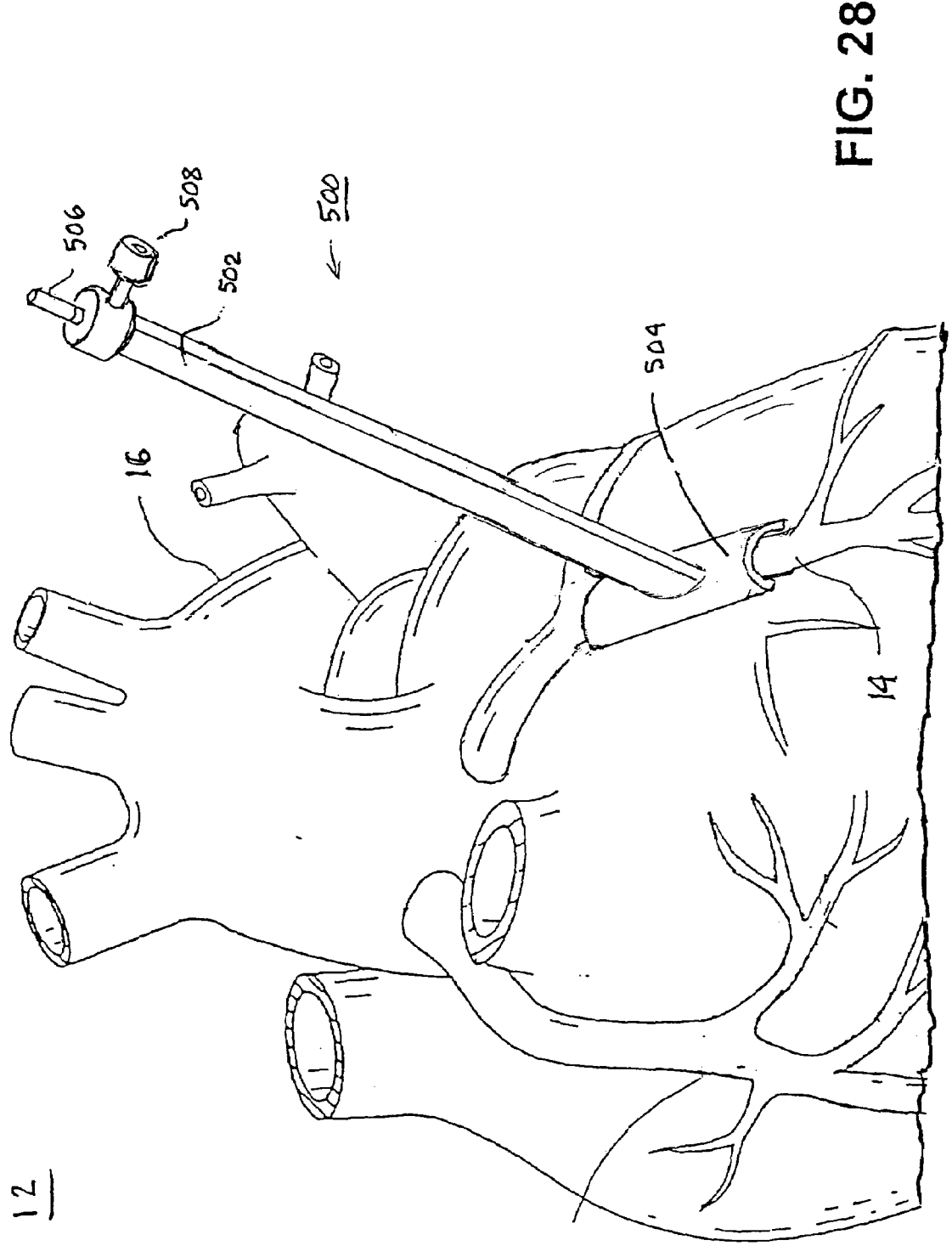
FIG. 28 is a schematic illustration of the application of a further embodiment of an electrosurgical vessel wail cutting tool of the invention applied to the outer surface of the wall of a coronary artery to create an arteriotomy as an area of the beating heart is immobilized by suction applied to the artery as RF energy is applied.

The arcuate suction pad 504 has open ends in the embodiments depicted in FIGS. 28–30. However, the ends can closed by end walls 518–520 as shown in the embodiment depicted in FIGS. 31 and 32 to provide the vessel occlusion function of the occlusion pads 496 and 498 of the electrosurgical tool 480 depicted in FIG. 27 and described above.

In use, the arcuate suction pad 504 and elongated electrosurgical cutting electrode 510 are aligned with the axis of the LAD coronary artery 14 (or other target vessel). The vacuum source creates suction between the vessel wall and the suction pad inner surface 512 to minimize vessel movement in the area around the site of the arteriotomy. RF energy is applied to the elongated electrosurgical cutting electrode 510 in the interval between heart contractions.

Figure 33:
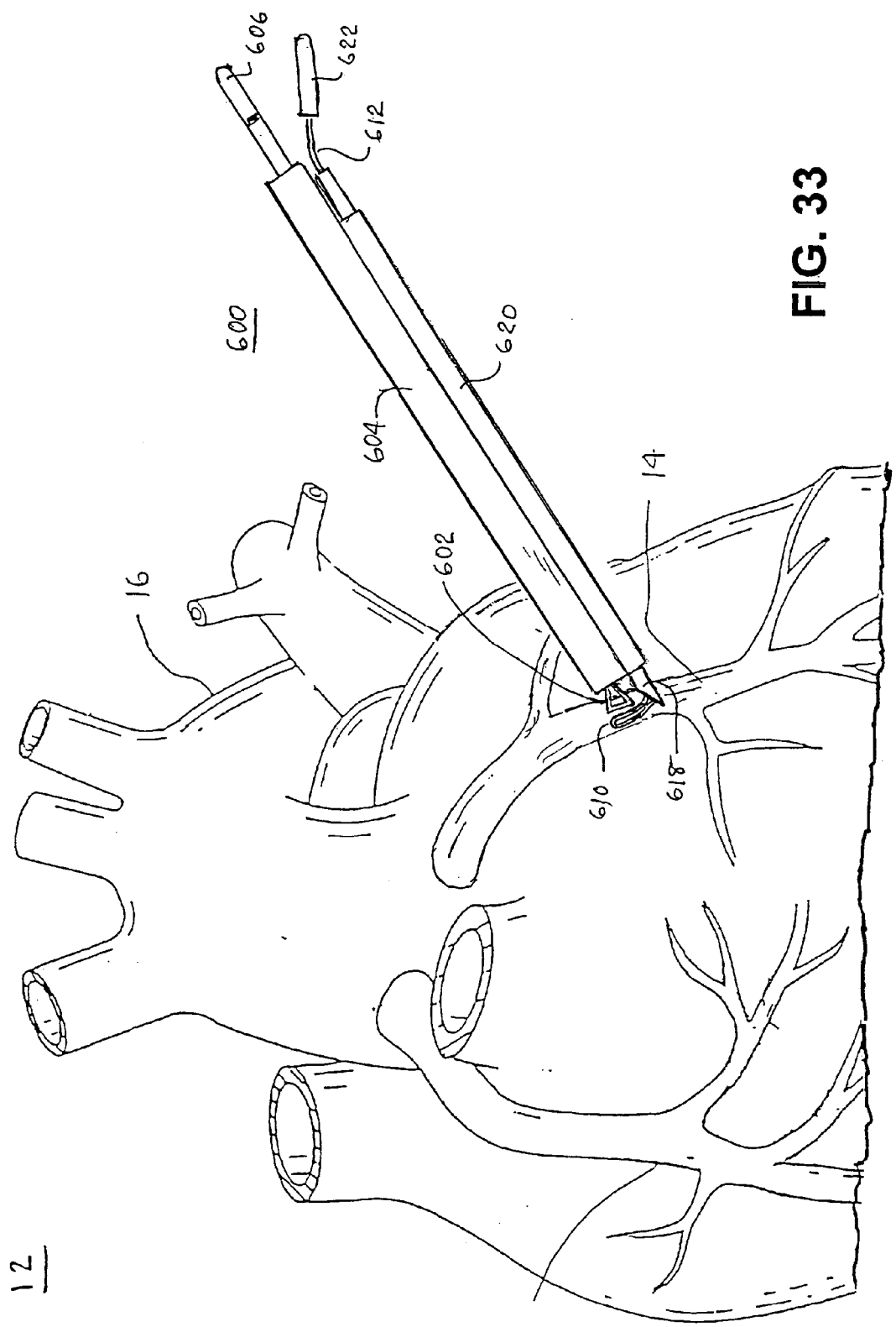
FIG. 33 is a schematic illustration of the application of a further embodiment of an electrosurgical vessel wall cutting tool of the invention applied to the outer surface of the wall of a coronary artery and a wire ground electrode introduced into the vessel lumen through a needle puncture of the vessel wall to create an arteriotomy as RF energy is applied.
Figure 34:
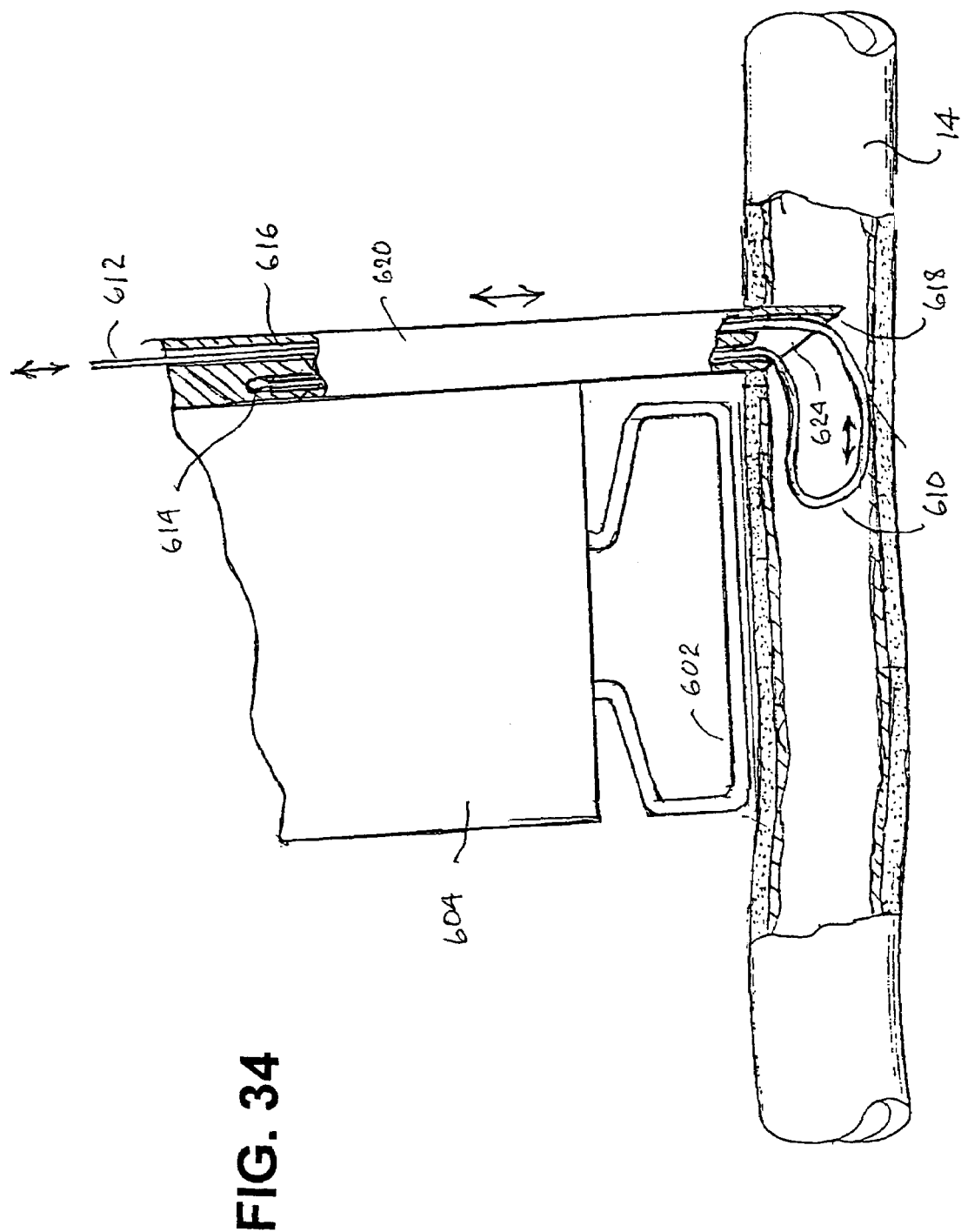
FIG. 34 is an enlarged detail view of the electrosurgical vessel wall cutting tool of FIG. 33 illustrating introduction of the ground wire into or retraction of the ground wire from the vessel lumen.
Figure 35:
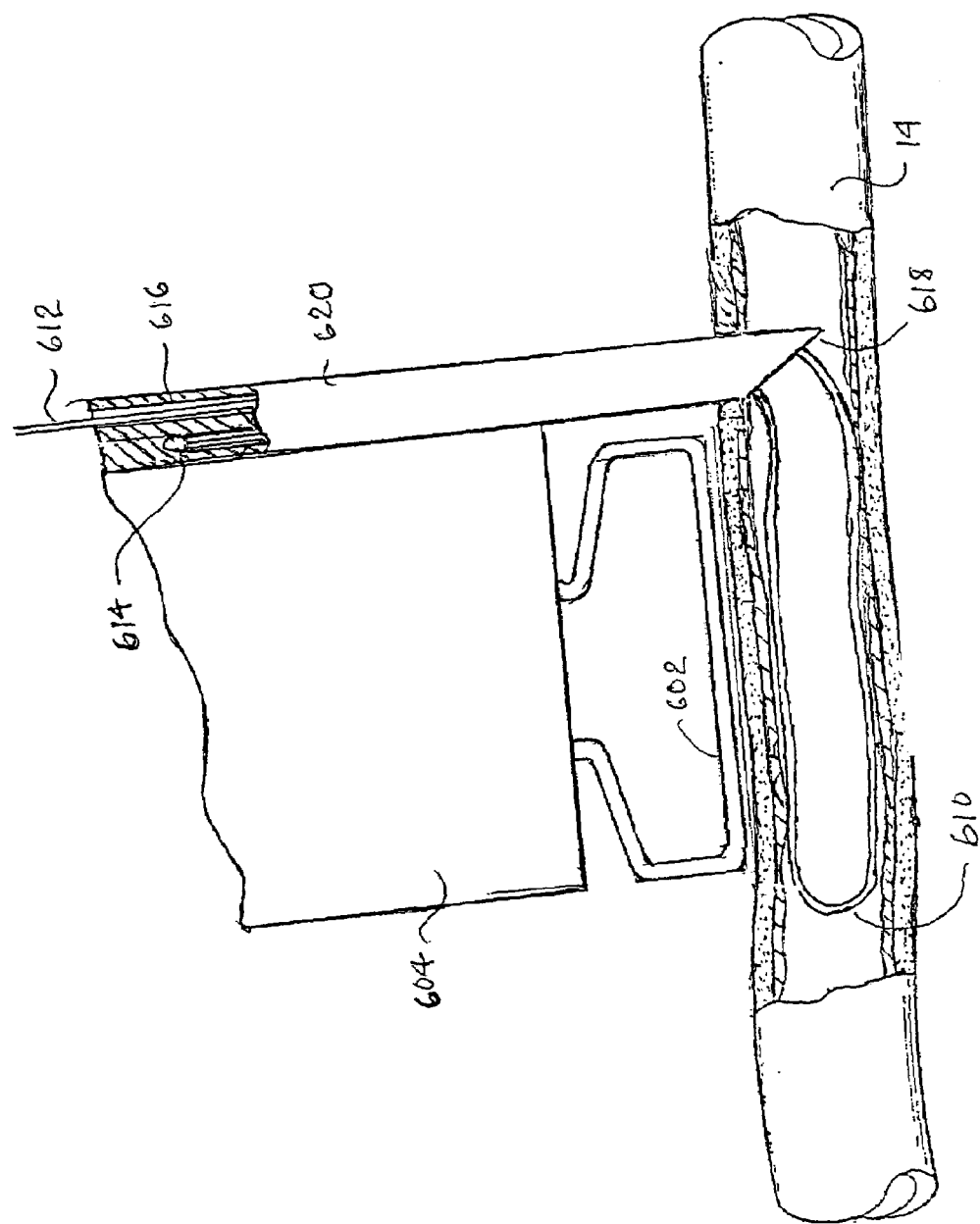
FIG. 35 is an enlarged detail view of the electrosurgical vessel wall cutting tool of FIG. 33 illustrating full introduction of the ground wire within the vessel lumen.

FIGS. 33–35 illustrate the principles of a further embodiment of an electrosurgical vessel wall cutting tool 600 operating in conjunction with a mechanism for delivering a wire ground electrode 610 into the vessel lumen through a needle puncture of the vessel wall. The mechanism for delivering a wire ground electrode 610 into the vessel lumen can be integrally incorporated with the tool body 604 as illustrated or can be separate from the tool body for use in any of the unipolar electrosurgical vessel wall cutting tools of the present invention. In this illustration, an arteriotomy is created in the LAD coronary artery 14 by RF energy applied between the elongated electrosurgical cutting electrode 602 and a wire ground electrode 610 when the wire ground electrode 610 is deployed within the artery lumen and the elongated electrosurgical cutting electrode 602 is applied to the arterial wall.

The elongated electrosurgical cutting electrode 602 is electrically connected to the connector element or pin 606 through a conductor extending through tool body 604. The elongated electrosurgical cutting electrode 602 can take any of the forms depicted in the figures.

The wire ground electrode 610 comprises a length of uninsulated or partially uninsulated, resilient wire 612 that can be extended out from or drawn into a lumen or pair of lumens 614 and 616 of a needle 620 having a vessel wall penetrating needle tip 618. One end of the wire 612 is fixed within the lumen 614 and the other free end of the wire 612 extends from the proximal end opening of the lumen 616 and is attached to a further connector element 622. A slot 624 is formed extending between the lumens 614 and 616 in the needle tip 618 as shown in FIG. 34. It will be understood that the needle 620 is expanded in relative size to the elongated electrosurgical cutting electrode 602 in the figures for ease in illustrating its features. Wire 612 may comprise one or more of a number of materials including nitinol, stainless, tungsten and titanium. The wire material may or may not be annealed.

In use, the free end of the wire 612 is pulled outward from the proximal end opening of the lumen 616 sufficiently to retract the wire loop through the lumen 616 and into slot 624 in the beveled needle tip 618. The beveled needle tip 618 is inserted through the vessel wall, and the free end of the wire 612 is advanced into the proximal end opening of the lumen 616 sufficiently to form and expand the wire loop from slot 624 in the beveled needle tip 618 as shown in FIG. 34 until the full sized wire loop is formed as shown in FIG. 35. The spring tension of the wire loop ensures that the sides of the loop are in intimate contact with opposite sides of the interior vessel wall. Thus, one side of the wire loop is in intimate contact with the interior vessel wall immediately across from the outer surface of the vessel wall that the elongated electrosurgical cutting electrode 602 is applied against. The RF energy generator is coupled with the connector elements 606 and 622, and an arteriotomy having a length equal to the length of the elongated electrosurgical cutting electrode 602 is created by application or RF energy between the elongated electrosurgical cutting electrode 602 and the wire ground electrode 610.

Automatic Switch

Figure 36:
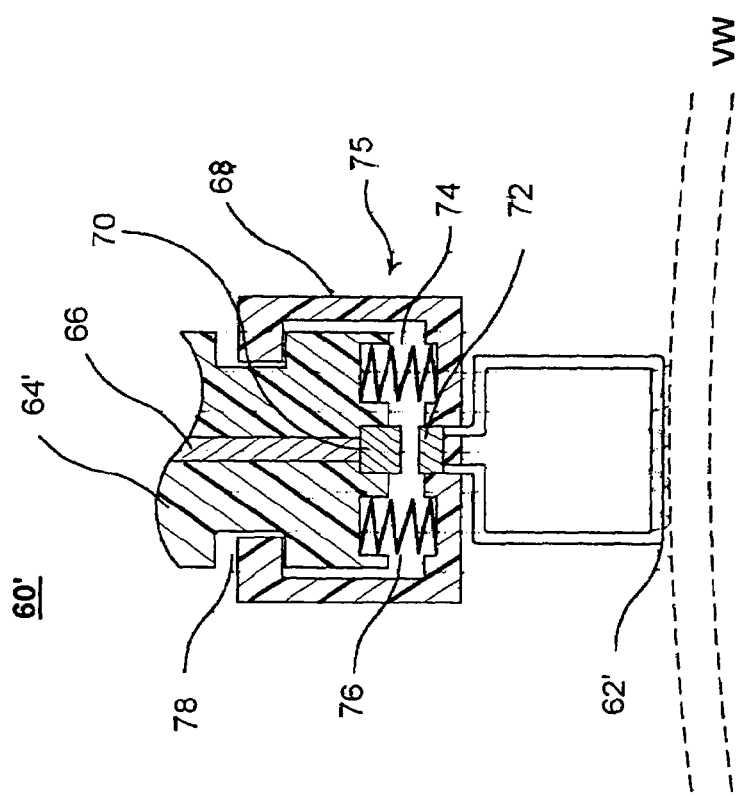
FIG. 36 is a partial cross-section view of the distal portion of a variation of the electrode head of the electrosurgical vessel wall cutting tools of the present invention incorporating a pressure responsive switch with the switch pads open.

In the above-described embodiments, it may be desirable to incorporate a pressure responsive mechanical switch within the tool bodies so that the RF energy can only be applied successfully when the elongated electrosurgical cutting electrode is in intimate contact with the vessel wall. Therefore, FIG. 36 schematically illustrate a universal electrosurgical tool 60' representing a possible modification of any the above-described electrosurgical tools having a spring loaded switch mechanism 75 incorporated between the tool body 64' and an end cap 68 that displaces the electrosurgical cutting electrode 62' from the tool conductor 66. The elongated electrode surgical cutting electrode 62' is represented as a wire loop electrode of the types described above but may take other forms, e.g., the elongated cutting electrode 510 of the electrosurgical vessel wall cutting tool 500.

In this embodiment, the tool conductor 66 terminates distally in a switch pad 70 centrally positioned at the distal end of tool body 64'. The loop ends of the electrosurgical cutting electrode 62' are joined together and to a switch pad 72 supported by the end cap 68 surrounding tool body 64'. An annular spring retention space is formed between the distal end of tool body 64' and the interior of the end cap 68. Either a single spring or the depicted plurality of springs 74, 76 are positioned and entrapped in the annular recess surrounding the switch pads 70 and 72. The end cap 68 and springs 74, 76 are entrapped by flange 78 extending inwardly into a groove of tool body 64' that limits relative displacement of the end cap 68 from the tool body 64'.

In use, the elongated electrosurgical cutting electrode 62' is normally disconnected from the conductor 66 by the force of the springs 74, 76 acting between the end cap 68 and tool body 64' as depicted in FIG. 36. Thus, RF energy applied that may be conducted through the conductor 66 will not be applied to the electrosurgical cutting electrode 62' if the electrosurgical cutting electrode 62' is only lightly in contact with or displaced from the vessel wall VW as shown in FIG. 36.

Figure 37:
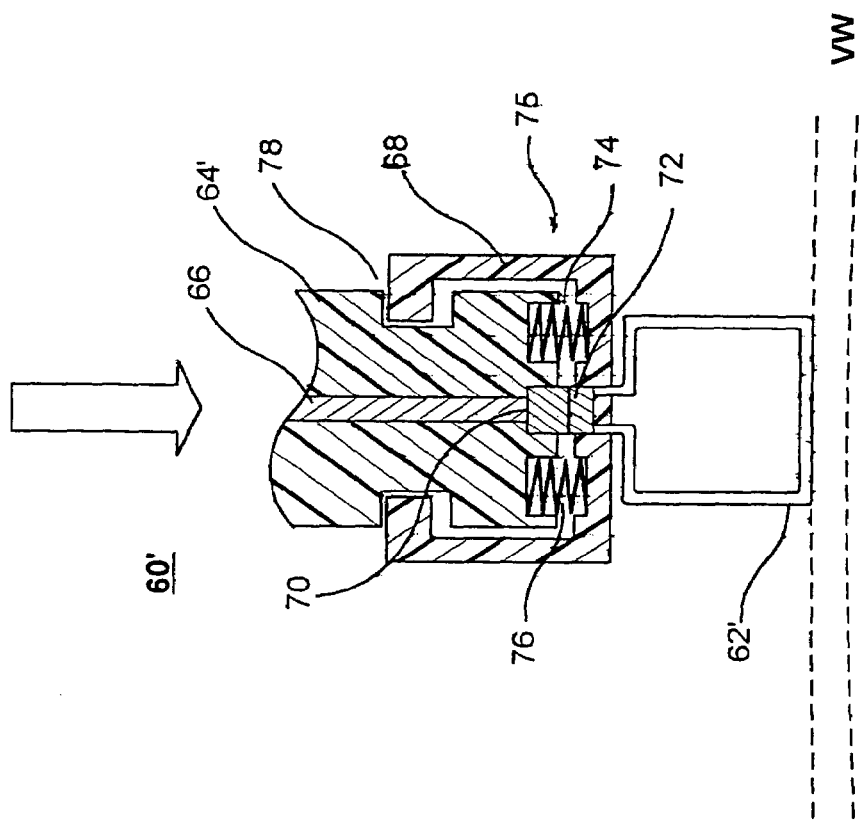
FIG. 37 is a partial cross-section view of the distal portion of a variation of the electrode head of the electrosurgical vessel wall cutting tools of the present invention incorporating a pressure responsive switch with the switch pads closed.

The elongated electrosurgical cutting electrode 62' is connected with the conductor 66 when the force of the springs 74, 76 acting between the end cap 68 and tool body 64' is overcome as depicted in FIG. 37. Thus, RF energy applied that may, be conducted through the conductor 66 can then be applied to the electrosurgical cutting electrode 62' as long as the electrosurgical cutting electrode 62' is firmly in contact with the vessel wall VW as shown in FIG. 37.

It will be understood that the RF energy generator coupled to the grounding pad or ground electrode 52 of FIG. 6 can be of the type that monitors current, voltage, series impedance and temperature and governs the application of RF energy. Thus, the state of the switch mechanism illustrated in FIGS. 33 and 34 can also be automatically monitored, and the physician can be provided with an indication that the switch pads 70, 72 are open or closed (i.e., in contact) when applying the electrosurgical cutting electrode 62' into contact with the vessel wall VW. The physician can then close the hand switch of the tool holder to apply the RF cutting energy when it is indicated that the switch pads are closed.

Figure 38:
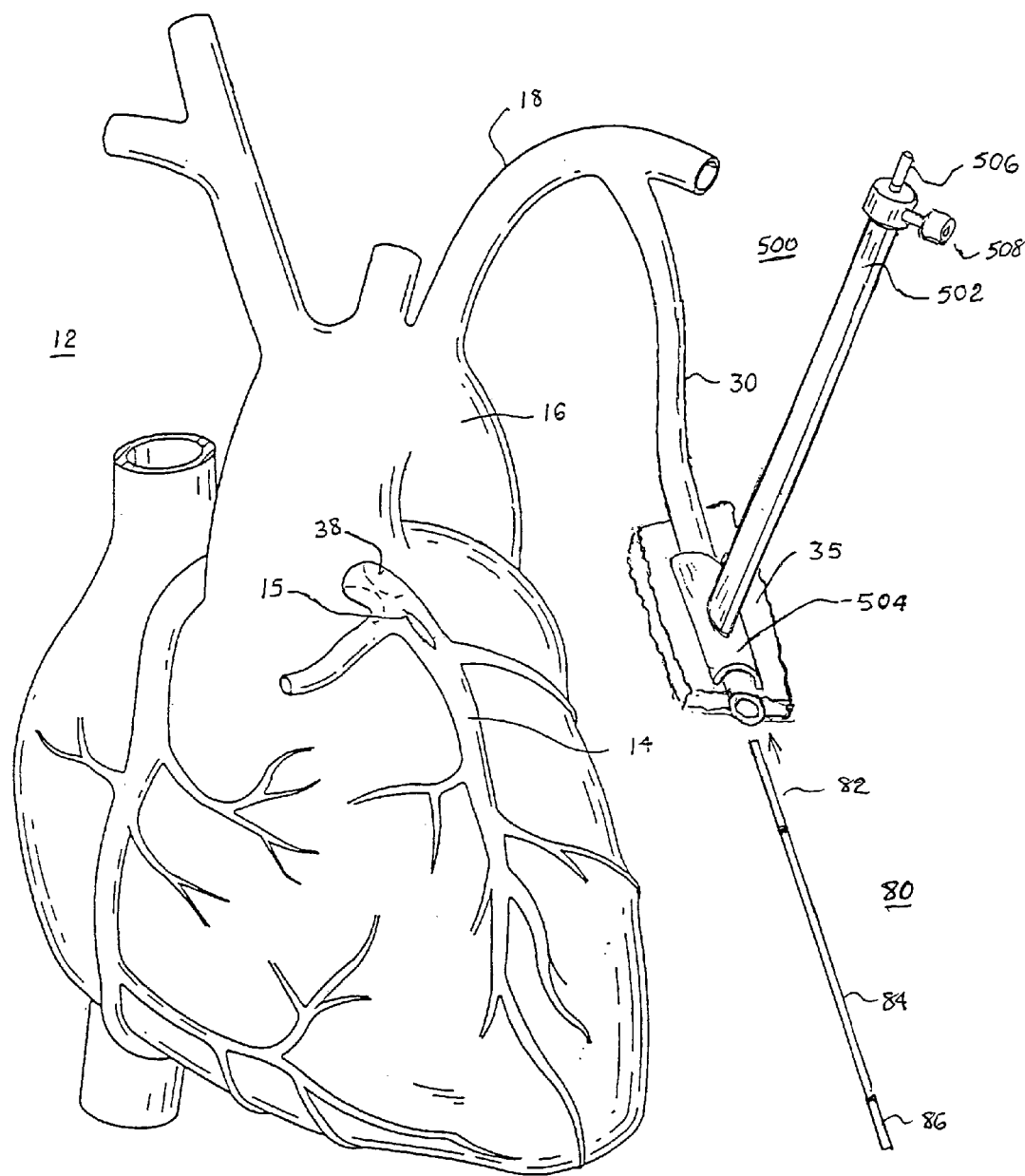
FIG. 38 is a schematic illustration of the application of the electrosurgical vessel wall cutting tool of FIG. 28 applied to the side wall of a source vessel to create an arteriotomy for a side-to-side anastomosis with a coronary artery.
Figure 39:
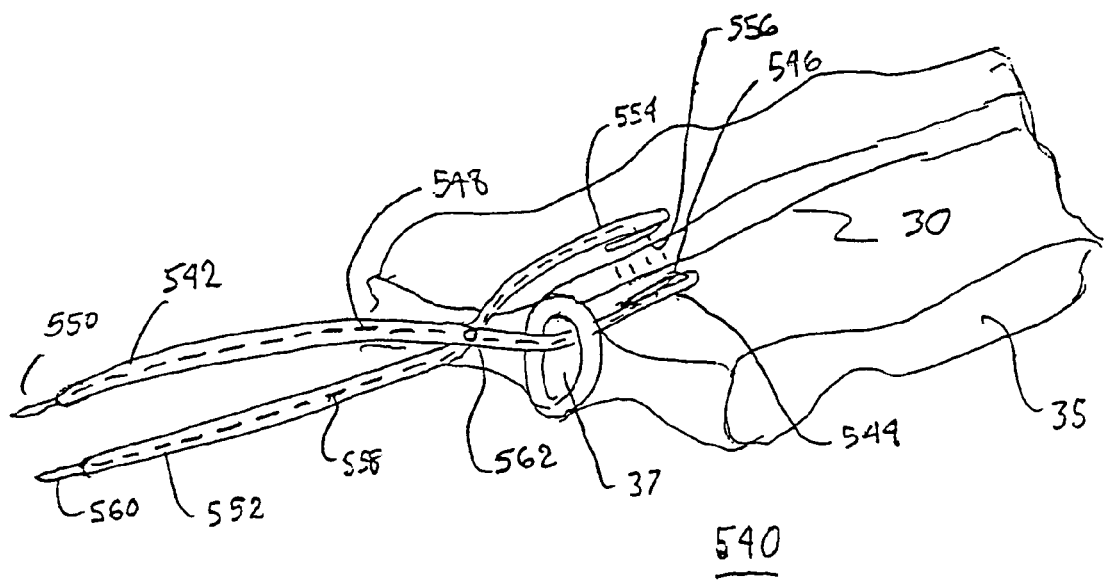
FIG. 39 is a schematic illustration of a further embodiment of an electrosurgical vessel wall cutting tool for forming an elongated slit in a source vessel to create an arteriotomy for a side-to-side anastomosis with a coronary artery.
Figure 40:
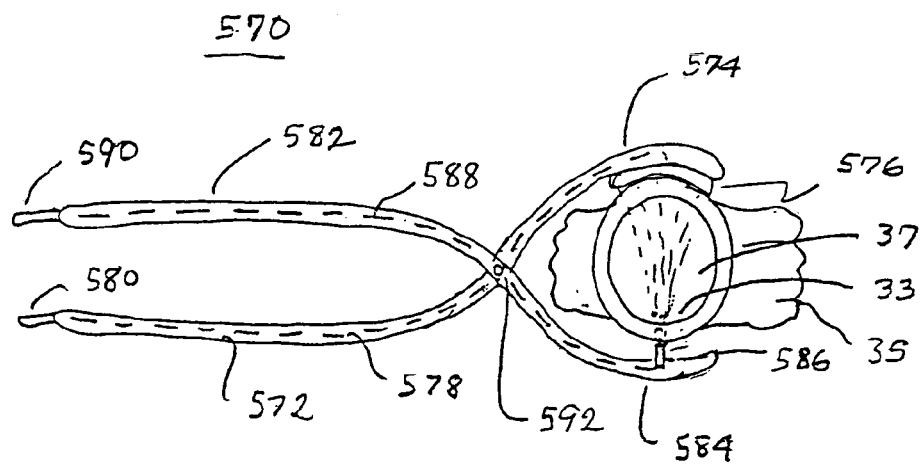
FIG. 40 is a schematic illustration of a still further embodiment of an electrosurgical vessel wall cutting tool for forming an elongated slit in a source vessel to create an arteriotomy for a side-to-side anastomosis with a coronary artery.
Figure 41:
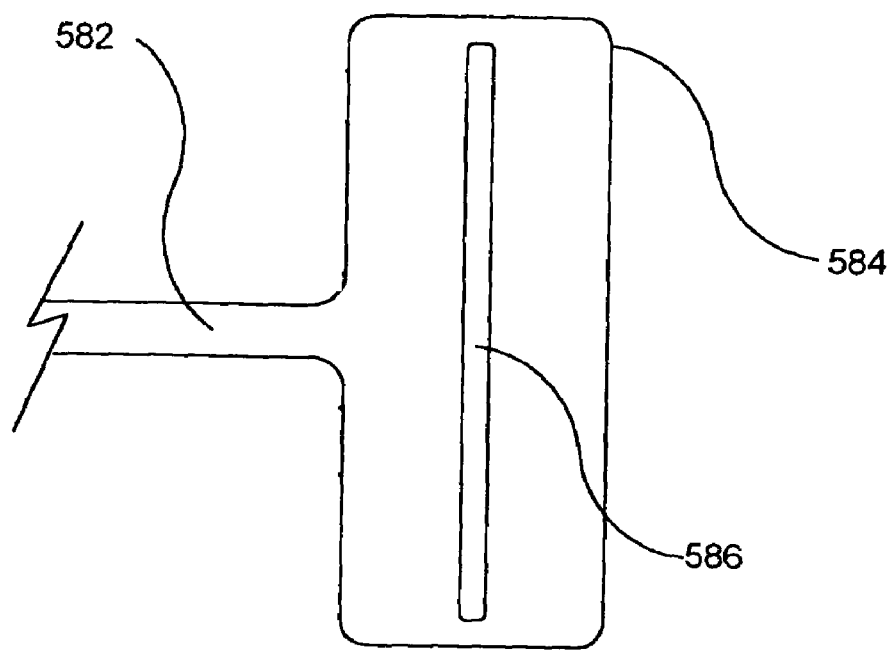
FIG. 41 is an enlarged detail view of the electrosurgical cutting electrode of the electrosurgical vessel wall cutting tool of FIG. 40.
Figure 42:
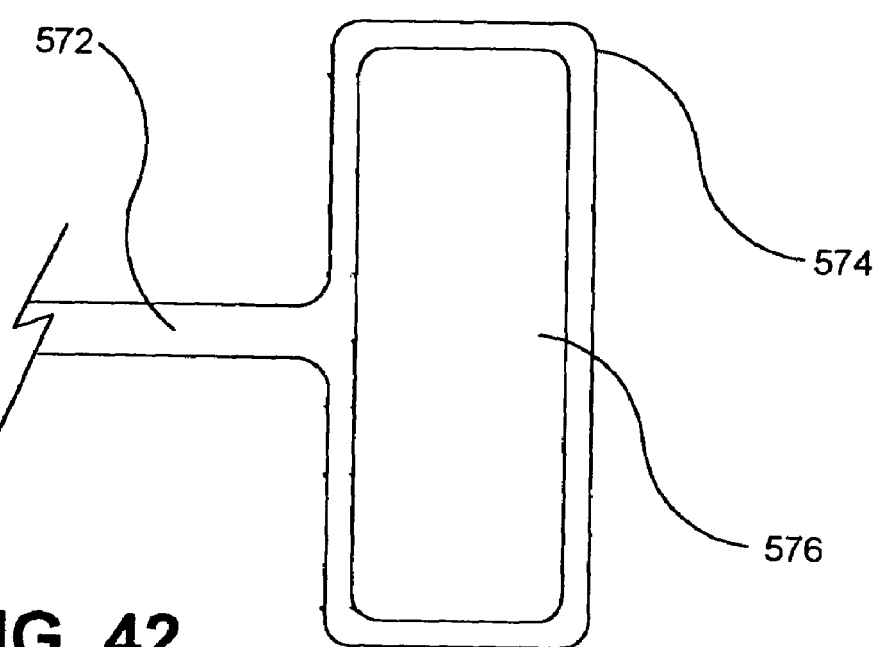
FIG. 42 is an enlarged detail view of the ground electrode of the electrosurgical vessel wall cutting tool of FIG. 40.

Source Vessel Arteriotomy for Side-to-Side Anastomosis:

Typically, the excised portion of the left IMA or right IMA, a radial artery or gastroepiploic artery is harvested within a flap of tissue referred to as a "pedicle" 35 as shown in FIG. 38. The pedicle 35 provides a small platform that can be grasped by forceps to position the vessel for making the side wall arteriotomy and during the completion of the anastomosis. Many of the above described unipolar, bipolar or multi-polar electrosurgical vessel wall cutting tools can be employed to make an arteriotomy in the sidewall of the surgically freed portion of the source vessel.

For example, FIG. 38 illustrates the use of the electrosurgical vessel wall cutting tool 500 against the vessel wall of the left IMA 30. The ground electrode 82 of a ground tool or wire 80 can be inserted into the lumen of the left IMA either by a trans-arterial route or through the open end electrode as depicted in FIG. 35 when a unipolar electrosurgical vessel wall cutting tool is employed. The wire body 84 can be inserted through an open chest or a closed chest, e.g., through a port or a cannula, or through a catheter, and the wire terminal 86 can be connected with the RF energy generator.

Further bipolar electrosurgical vessel wall cutting tools 540 and 570 are schematically depicted in FIGS. 39–42 that can be advantageously used to form an arteriotomy in the side wall of a vessel, e.g., the illustrated left IMA 30. The electrosurgical vessel wall cutting tools 540 and 570 are configured as forceps having forceps handles coupled together by a swivel pin and having active and ground RF electrodes formed on the jaw surfaces that face one another and can be brought together or apart by movement of the forceps handles.

The electrosurgical vessel wall cutting tool 540 comprises a first handle 542 and a second handle 552 joined together at a swivel pin 562. Handle 542 extends to a first jaw 544 supporting an elongated exposed electrode 546 that can be used either as an electrosurgical cutting or ground electrode.

A conductor 548 enclosed within the handle 542 extends between the elongated electrosurgical cutting or ground electrode 546 and a connector pin 550 adapted to be attached by a cable to either the active or ground output terminal of an RF energy generator. Similarly, second handle 552 extends to a second jaw 554 supporting an elongated electrosurgical cutting or ground electrode 556. A conductor 558 enclosed within the handle 552 extends between the elongated electrosurgical cutting or ground electrode 556 and a connector pin 560 adapted to be attached by a cable to either the active or ground output terminal of an RF energy generator.

In use, cables from the RF energy generator output terminals are coupled to the connector pins 550 and 560. First jaw 544, for example, is inserted axially through the open cut end and into the lumen 37 of the left IMA 30 to present the electrode 546 against the inner surface of the vessel wall and the electrode 556 against the outer surface of the vessel wall. The RF energy is applied through the vessel wall between the opposed electrodes 546 and 556 to cut away the vessel wall and form the arteriotomy, e.g., arteriotomy 33 depicted in FIG. 3. The length of the arteriotomy can be either dictated by the lengths of the opposed electrodes 546 and 556 or made longer by moving the jaws 544, 554 and successively cutting the vessel wall until a desired length is achieved.

The electrosurgical vessel wall cutting tool 570 also comprises a first handle 572 and a second handle 582 joined together at a swivel pin 592. First handle 572 extends to a somewhat arcuate first jaw 574 supporting an elongated, exposed, electrosurgical ground electrode 576 that is intended to be applied against the exposed outer surface of the vessel wall on one side of the pedicle 35. A conductor 578 enclosed within the handle 572 extends between the elongated electrosurgical ground electrode 576 and a connector pin 580 adapted to be attached by a cable to the ground output terminal of an RF energy generator. Similarly, second handle 582 extends to a somewhat arcuate second jaw 584 supporting an elongated electrosurgical cutting electrode 586 adapted to be applied against the outer surface of the vessel wall on the other side of the pedicle 35. A conductor 588 enclosed within the handle 582 extends between the elongated eletrosurgical cutting electrode 586 and a connector pin 590 adapted to be attached by a cable to the active output terminal of an RF energy generator.

In this embodiment, the electrosurgical cutting electrode 586 and the supporting jaw 584 are elongated in the axial direction of the vessel such that the axial length of the electrosurgical cutting electrode 586 defines the length of the arteriotomy 33 parallel to the vessel axis. The electrosurgical ground electrode 576 may be the same length and wider than the electrosurgical cutting electrode 586 so that the surface area of the electrosurgical ground electrode 576 exceeds surface area of the electrosurgical cutting electrode 586 to concentrate current density at the electrosurgical cutting electrode 586 and reduce current density at the electrosurgical ground electrode 576.

In use, cables from the RF energy generator output terminals are coupled to the connector pins 580 and 590. Jaws 574 and 584 are applied to either side of the vessel wall exposed from the pedicle 35. The RF energy is applied through the vessel wall between the opposed electrodes 586 and 576 to cut away the vessel wall and form the arteriotomy, e.g., arteriotomy 33 depicted in FIG. 3. The RF energy is concentrated along the length and width of the elongated electrosurgical cutting electrode 586 to cut the arteriotomy 33 only in the vessel wall contacted by the electrosurgical cutting electrode 586.

Figure 43:
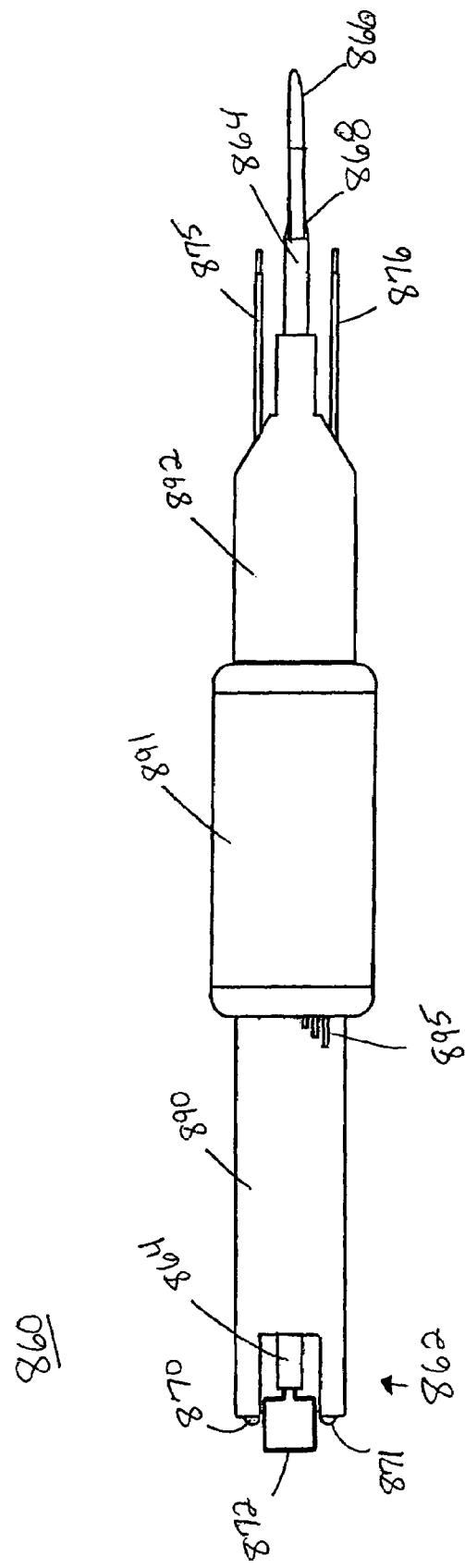
FIG. 43 is a further embodiment of an electrosurgical vessel wall cutting tool having sensing electrodes for forming an elongated slit in a source vessel to create an arteriotomy.
Figure 44:
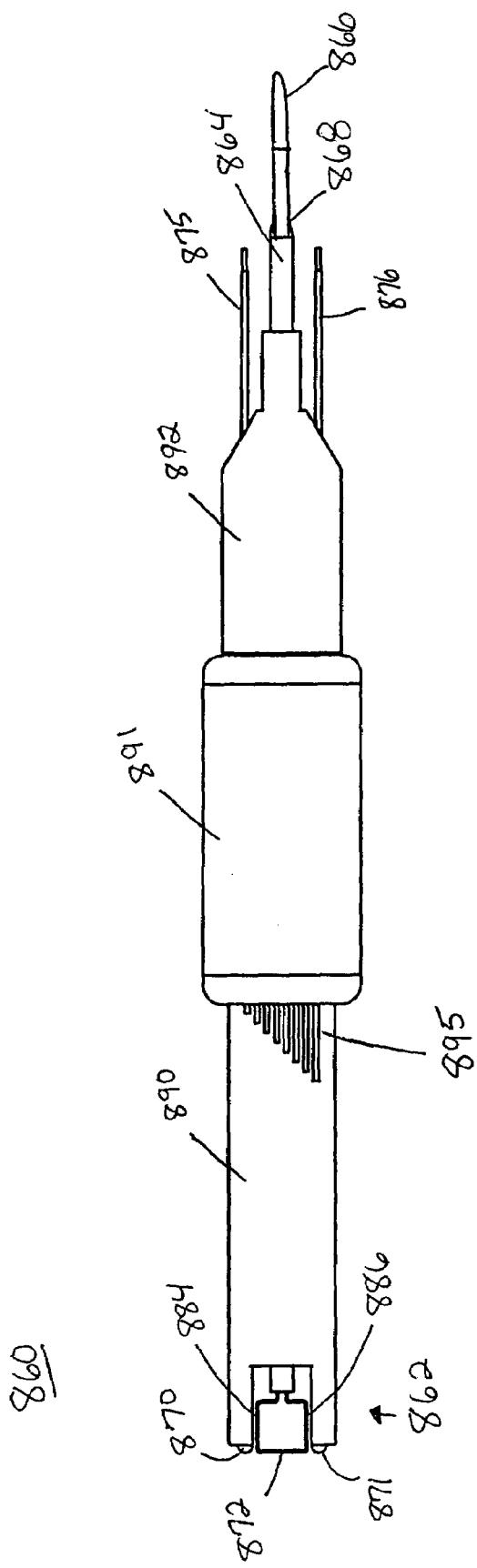
FIG. 44 is another view of the electrosurgical vessel wall cutting tool of FIG. 43.

Another preferred embodiment of an electrosurgical vessel wall cutting tool 860 is depicted in FIGS. 43 and 44. The unipolar (i.e., single electrode) electrosurgical vessel wall cutting tool 860 has an elongated conducting tool body 868 extending between the distal cutting head 862 and a proximal connector pin 866. Tool body 868 is suitably long enough to be extended through an incision or port 34 or 36 to apply the distal cutting head 862 in operative relation to the selected arteriotomy site. Tool body 868 is preferably a metal conducting tube.

The distal cutting head 862 comprises a pair of tissue sensing electrodes 870 and 871 adjacent an elongated electrosurgical cutting electrode 872 that can be applied against the outer surface of a vessel or arterial wall. The sensing electrodes 870 and 871 stop advancement of the elongated electrosurgical cutting electrode 872 into the vessel as well as control the output of RF energy so as to lessen the likelihood that the elongated electrosurgical cutting electrode 872 would be pressed all the way through the vessel lumen and against the opposite side wall of the vessel, thereby preventing the overheating of tissue located on the opposite side wall of the vessel. Sensing electrodes 870 and 871 are coupled to conductors 875 and 876, respectively. During use of device 860, conductors 875 and 876 are coupled to a signal generating source (not shown).

The signal generator is capable of producing a sufficiently high frequency signal to sensing electrodes 870 and 871 so as not to cause the stimulation of cardiac tissue, if so desired. An electrical characteristic such as impedance of the series circuit between tissue sensing electrodes 870 and 871 is monitored during application of RF energy to cutting electrode 872. The sudden change in an electrical characteristic such as impedance as the tissue sensing electrodes contact tissue is detected and employed to signal completion and/or to automatically terminate the RF energy. For example, the RF energy is automatically cut-off when sensing electrodes 870 and/or 871 come into contact with tissue. Elongated wire, cutting electrode 872 is supported at the end of tool body 868 by a pair of electrode support legs 884 and 886 that are electrically connected together and to the distal end of tool body 868 extending through an insulating sheath 864 to the proximal connector pin 866. Insulating sheath 864 comprises an insulating material that at least partially surrounds the conducting tool body 868. The connector pin 866 receives and is crimped or welded over a proximal end portion of the conducting tool body 868. The distal end of tool body 868 is coupled to the distally extending ends of the elongated electrosurgical cutting electrode 872 by way of a crimp.

The elongated electrosurgical cutting electrode 872 may be nominally oriented 900 to the axis of tool body 868. The elongated electrosurgical cutting electrode 872 can be a 5 mm×5 mm square loop of tungsten metal, e.g., the Model LLETZ Loop Electrode available from Valleylab, Inc., of Boulder, Colo. It will be understood that the elongated electrosurgical cutting electrode 872 can have alternative shapes, e.g., a "V-shape" or a "L-shape" whereby the elongated electrosurgical cutting electrode 872 is supported by only one of the legs 884 or 886.

Figure 45:
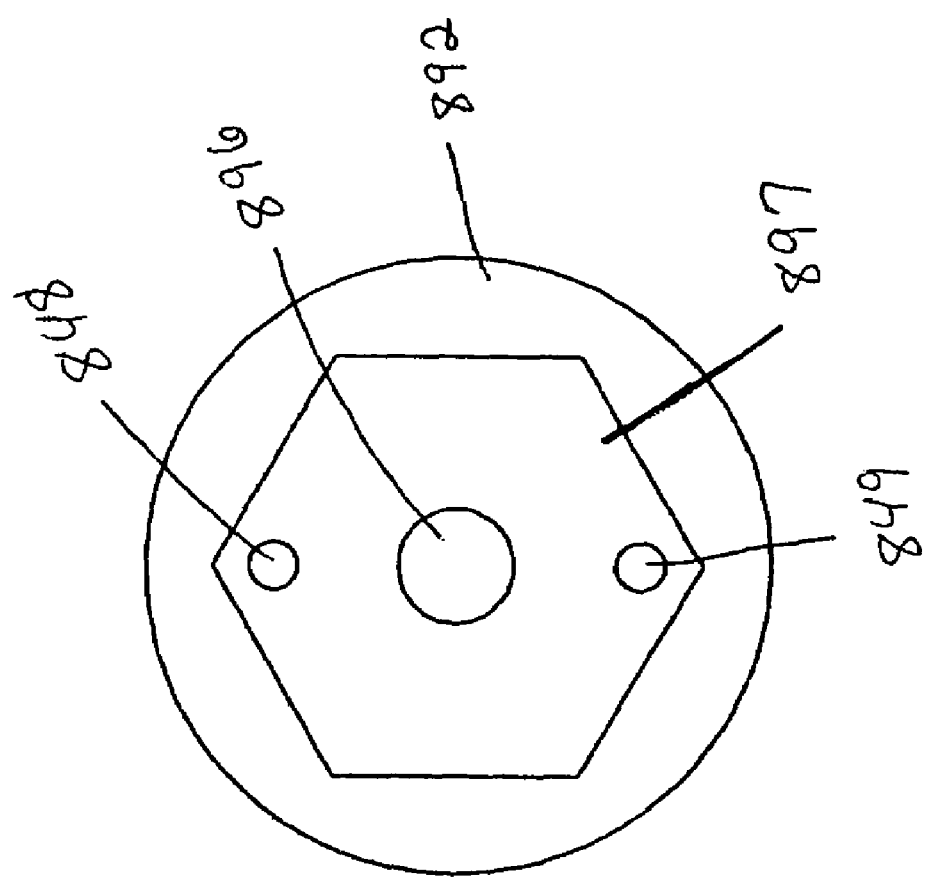
FIG. 45 is an end view of a portion of the electrosurgical vessel wall cutting tool of FIG. 43.

Tool body 868 is fixed within lumen 896 of tool member 892 while conductors 875 and 876 pass through lumens 848 and 849, respectively (see FIG. 45). In addition, tool member 892 has a recessed space or slot 897 at its proximal end for receiving the distal end of tool member 890. Tool member 892 and tool member 890 preferably fit together movably wherein the distal end of tool member 890 can slide back and forth within the proximal end of tool member 892. The fit between tool members 890 and 892 is designed so that members 890 and 892 will not rotate relative to each other. One method for allowing linear travel but not rotational travel between members 890 and 892 is to use a keyed slot design. For example, providing a multi-sided shape, e.g., a hexagon, to the distal end of member 890 and the corresponding multi-sided shaped slot within the proximal end of member 892 allows linear travel but not rotational travel between the two members. Tool members 890 and 892 are preferably made of an insulating or non-conducting material.

Figure 46:
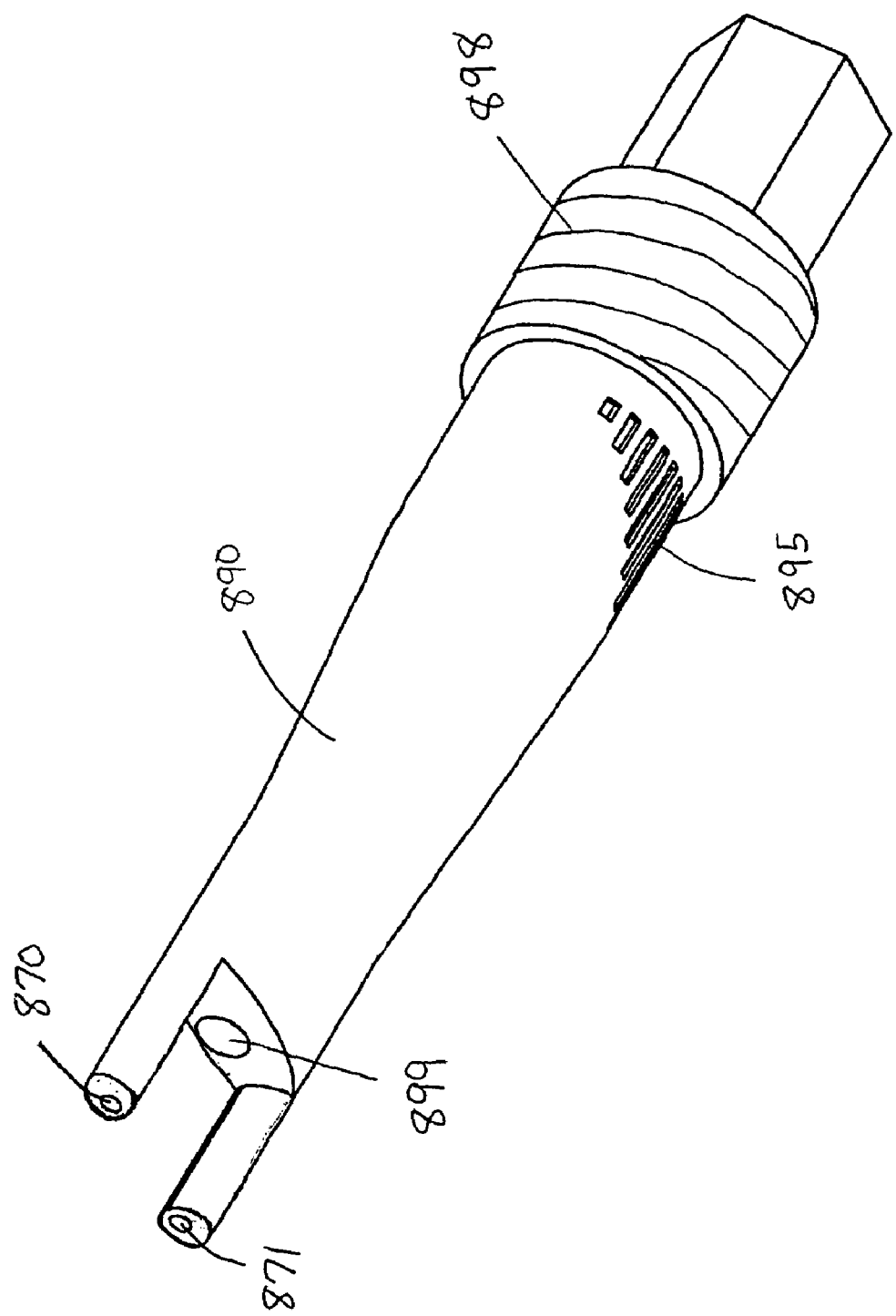
FIG. 46 is a side view of a portion of the electrosurgical vessel wall cutting tool of FIG. 43.

The distal end of tool member 891 is coupled movably to the proximal end of tool member 892. Tool member 891 is allowed to rotate around the proximal end of tool member 892 but is not allowed to travel linear relative to tool member 892. The proximal end of tool member 891 is threaded onto threads 898 (see FIG. 46) of tool member 890. A portion of tool body 868 resides movably within lumen 899 of tool member 890. Rotating tool member 891 around tool member 892 causes tool member 890 to travel in a linear fashion relative to tool members 891 and 892 as well as tool body 868, thereby allowing a physician to selectively move sensing electrodes 870 and 871 relative to cutting electrode 872 via rotation of tool member 891. Sensing electrodes 870 and 871 are both fixed to tool member 890. An indicator, e.g., a scale 895 on tool member 890, may be used to provide information to the physician about the distance between sensing electrodes 870 and 871 and cutting electrode 872, thereby allowing the physician to dial-in the appropriate cut depth. A variety of indicators may be used to indicate to the physician a selected cutting depth. For example, an electronic indicator may be used.

A variety of techniques or means may be employed for controlling the cutting depth of device 860. Tissue activated switches for shutting off or modulating RF energy output when a desired cut depth is reached may be employed. For example, one or more sensors, electrical sensors, fiber optic sensors, proximity sensors that measure conductance and/or mechanical switches may be used. For example, sensing electrodes 870 and 871 of device 860 may be replaced with one or more small mechanically activated switches. When the mechanical switches are pushed against tissue they become activated thereby shutting off the RF energy being supplied to cutting electrode 872. In addition, sensors that can identify different tissue types may be used to modulate the output of RF energy. For example, fatty tissue has different impedance than vessel wall tissue. Sensors designed to sense difference in impedance, e.g., sensing electrodes 870 and 871, may be used to change the RF energy output to cutting electrode 872 based on the type of tissue being cut.

It will be understood that the electrosurgical vessel wall cutting tool 860 depicted in FIGS. 43 and 44 can be employed through a small chest incision with or without use of a port in the percutanous procedure depicted in FIG. 5 as well as in any of the other more invasive surgical procedures to access heart 12 described above and wherein the heart 12 is either stopped or is beating and stabilized as described further herein. For example, in one embodiment of the present invention, tool member 890 and tool body 868 may be suitably long enough to be extended through a small incision or port 34 or 36 to apply the distal cutting head 862 in operative relation to the selected arteriotomy site.

It will also be understood that a ground pad contacting the patient's skin or a ground wire as described above may be used with electrosurgical vessel wall cutting tool 860. For example, a return or ground electrode may be introduced into the lumen of the vessel, e.g., LAD coronary artery 14, into close proximity with the cutting electrode 872 at the distal cutting head 862. RF energy is then applied through the elongated electrosurgical cutting electrode and the return or ground electrode.

Conclusion

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of electrosurgical instruments and electrosurgery that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

The invention claimed is:

1. A method of making an elongated slit through a vessel wall and into a lumen of a body vessel, having a body vessel axis, of a patient comprising the steps of:

obtaining access to a surface of the vessel wall;

applying a ground electrode in contact with the body of the patient;

applying an elongated electrosurgical cutting electrode to the surface of the vessel wall in substantially parallel alignment with the body vessel axis, the elongated electrosurgical cutting electrode having a predetermined cutting electrode length exceeding the cutting electrode width, wherein the step of applying a ground electrode further comprises introducing the ground electrode into the lumen of the body vessel in proximity with the elongated electrosurgical cutting electrode applied to an outer surface of the vessel wall; and applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

2. The method of claim 1, wherein the step of applying a ground electrode further comprises introducing the ground electrode through the vessel wall and into the lumen of the body vessel in proximity with the elongated electrosurgical cutting electrode applied to the outer surface of the vessel wall.

3. The method of claim 2, wherein the ground electrode comprises an elongated wire extending to a wire tip and the introducing step comprises advancing the wire tip through the vessel wall.

4. A method of making an elongated slit through a vessel wall and into a lumen of a body vessel, having a body vessel axis, of a patient comprising the steps of:
  obtaining access to a surface of the vessel wall;
  applying a ground electrode in contact with the body of the patient;
  applying an elongated electrosurgical cutting electrode to the surface of the vessel wall in substantially parallel alignment with the body vessel axis, the elongated electrosurgical cutting electrode having a predetermined cutting electrode length exceeding the cutting electrode width, wherein the step of applying a ground electrode further comprises applying an elongated ground electrode against an outer surface of the vessel wall substantially in parallel with the elongated electrosurgical cutting electrode applied to the outer surface of the vessel wall; and
  applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

5. The method of claim 4, wherein the step of applying a ground electrode further comprises applying first and second elongated ground electrodes against an outer surface of the vessel wall substantially in parallel with and along each side of the elongated electrosurgical cutting electrode applied to the outer surface of the vessel wall.

6. A method of making an elongated slit through a vessel wall and into a lumen of a body vessel, having a body vessel axis, of a patient comprising the steps of:
  obtaining access to a surface of the vessel wall;
  applying a ground electrode in contact with the body of the patient;
  applying an elongated electrosurgical cutting electrode to the surface of the vessel wall in substantially parallel alignment with the body vessel axis, the elongated electrosurgical cutting electrode having a predetermined cutting electrode length exceeding the cutting electrode width, wherein the step of applying a ground electrode further comprises:
  providing an elongated ground wire having an exposed ground electrode;
  transcutaneously obtaining access to the patient's vascular system; and
  introducing the ground wire through the access to the vascular system and the vasculature to locate the ground electrode within the lumen of the body vessel and in proximity with the elongated electrosurgical cutting electrode applied to an outer surface of the vessel wall; and
  applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

7. A method of making an elongated slit through a vessel wall and into a lumen of a body vessel, having a body vessel axis, of a patient comprising the steps of:
  obtaining access to a surface of the vessel wall;
  applying a ground electrode in contact with the body of the patient;
  applying an elongated electrosurgical cutting electrode to the surface of the vessel wall in substantially parallel alignment with the body vessel axis, the elongated electrosurgical cutting electrode having a predetermined cutting electrode length exceeding the cutting electrode width, wherein the step of applying a ground electrode further comprises:
  providing an elongated ground wire having an exposed ground electrode;
  introducing the ground wire through the vessel wall; and
  forming the ground wire into a wire loop within the vessel lumen that applies at least a section of the wire loop against the interior surface of the vessel wall in proximity with the elongated electrosurgical cutting electrode applied to an outer surface of the vessel wall; and
  applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

8. A method of making an elongated slit through a vessel wall and into a lumen of a body vessel, having a body vessel axis, of a patient comprising the steps of:
  obtaining access to a surface of the vessel wall;
  applying a ground electrode in contact with the body of the patient;
  applying an elongated electrosurgical cutting electrode to the surface of the vessel wall in substantially parallel alignment with the body vessel axis, the elongated electrosurgical cutting electrode having a predetermined cutting electrode length exceeding the cutting electrode width;
  applying suction to the body vessel to stabilize the body vessel from movement and to maintain the elongated electrosurgical cutting electrode in contact with the surface of the body vessel; and
  applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

9. A method of making an elongated slit through a vessel wall and into a lumen of a body vessel, having a body vessel axis, of a patient comprising the steps of:
  obtaining access to a surface of the vessel wall, wherein the body vessel is supported by body tissue;
  applying a ground electrode in contact with the body of the patient;
  applying an elongated electrosurgical cutting electrode to the surface of the vessel wall in substantially parallel alignment with the body vessel axis, the elongated electrosurgical cutting electrode having a predetermined cutting electrode length exceeding the cutting electrode width;
  applying suction to the body tissue alongside the body vessel to stabilize the body vessel from movement and to maintain the elongated electrosurgical cutting electrode in contact with the surface of the body vessel; and
  applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

10. A method of making an elongated slit through a vessel wall and into a lumen of a body vessel, having a body vessel axis, of a patient comprising the steps of:
- obtaining access to a surface of the vessel wall, wherein the body vessel is supported by body tissue;
- applying a ground electrode in contact with the body of the patient;
- applying an elongated electrosurgical cutting electrode to the surface of the vessel wall in substantially parallel alignment with the body vessel axis, the elongated electrosurgical cutting electrode having a predetermined cutting electrode length exceeding the cutting electrode width;
- applying force against the body tissue alongside the body vessel to stabilize the body vessel from movement and to maintain the elongated electrosurgical cutting electrode in contact with the surface of the body vessel; and
- applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

11. The method of claim 10, wherein the elongated electrosurgical cutting electrode is applied to an outer surface of the vessel wall.

12. The method of claim 10, wherein the body vessel is a coronary artery supported upon the epicardium of the heart and the step of obtaining access to the body vessel comprises surgically accessing the epicardium of the heart through a minimally invasive surgical incision through the chest wall.

13. A method of making an elongated slit through a vessel wall and into a lumen of a body vessel, having a body vessel axis, of a patient comprising the steps of:
- obtaining access to a surface of the vessel wall, wherein the body vessel is supported by body tissue;
- applying a ground electrode in contact with the body of the patient;
- applying an elongated electrosurgical cutting electrode to the surface of the vessel wall in substantially parallel alignment with the body vessel axis, the elongated electrosurgical cutting electrode having a predetermined cutting electrode length exceeding the cutting electrode width and the elongated electrosurgical cutting electrode is mounted within a stop and the step of applying the elongated electrosurgical cutting electrode to a surface of the vessel wall further comprises stopping the advancement of the elongated electrosurgical cutting electrode into the vessel lumen through contact of the stop against the body tissue supporting the body vessel; and
- applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

14. A method of making an elongated slit through a vessel wall and into a lumen of a body vessel, having a body vessel axis, of a patient comprising the steps of:
- obtaining access to a surface of the vessel wall, wherein the body vessel is a blood vessel supported by body tissue containing blood;
- applying a ground electrode in contact with the body of the patient;
- applying an elongated electrosurgical cutting electrode to the surface of the vessel wall in substantially parallel alignment with the body vessel axis, the elongated electrosurgical cutting electrode having a predetermined cutting electrode length exceeding the cutting electrode width;
- applying RF energy between the electrosurgical cutting electrode and the ground electrode at an energy level and for a duration sufficient to cut an elongated slit through the vessel wall where the elongated electrosurgical cutting electrode is applied to the surface of the vessel wall; and
- applying an occlusion frame against the blood vessel and body tissue to compress the blood vessel lumen and inhibit blood loss through the elongated slit.

15. A method of making an elongated slit through a vessel wall and into a lumen of a body vessel, having a body vessel axis, of a patient comprising the steps of:
- obtaining access to a surface of the vessel wall;
- applying a ground electrode in contact with the body of the patient;
- applying an elongated electrosurgical cutting electrode to the surface of the vessel wall in substantially parallel alignment with the body vessel axis, the elongated electrosurgical cutting electrode having a predetermined cutting electrode length exceeding the cutting electrode width, wherein the elongated electrosurgical cutting electrode is mounted to an elongated tool body of an electrosurgical vessel wall cutting tool to nominally extend at a predetermined angle to an elongated axis of the elongated tool body and the step of applying the elongated electrosurgical cutting electrode to a surface of the vessel wall further comprises:
- adjusting the predetermined angle to allow the elongated electrosurgical cutting electrode to be placed in alignment with the axis of the body vessel and in contact with the outer surface of the vessel wall; and
- applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

16. A method of making an elongated slit through a vessel wall and into a lumen of a body vessel, having a body vessel axis, of a patient comprising the steps of:
- obtaining access to a surface of the vessel wall, wherein the body vessel is supported by body tissue;
- providing a tool body including a forceps having first and second opposable jaws coupled to first and second handles, respectively, the forceps supporting a ground electrode on the first jaw and an elongated electrosurgical cutting electrode on the second jaw;
- surgically dissecting a section of the body vessel from the body tissue and forming an opening in the body vessel to expose the vessel lumen
- applying the ground electrode in contact with the body of the patient comprising inserting the first jaw through the vessel wall opening into the vessel lumen;
- applying the elongated electrosurgical cutting electrode to the surface of the vessel wall in substantially parallel alignment with the body vessel axis, the elongated electrosurgical cutting electrode having a predetermined cutting electrode length exceeding the cutting electrode width, the step of applying the elongated electrosurgical cutting electrode in contact with the surface of the vessel wall comprises bringing the first and second opposable jaws together; and applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

17. A method of making an elongated slit through a vessel wall and into a lumen of a body vessel, having a body vessel axis, of a patient comprising the steps of:
   obtaining access to a surface of the vessel wall;
   applying a ground electrode in contact with the body of the patient;
   applying an elongated electrosurgical cutting electrode to an inner surface of the vessel wall in substantially parallel alignment with the body vessel axis, the elongated electrosurgical cutting electrode having a predetermined cutting electrode length exceeding the cutting electrode width; and
   applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

18. A method of making an elongated slit through a vessel wall and into a lumen of a body vessel, having a body vessel axis, of a patient comprising the steps of:
   obtaining access to a surface of the vessel wall, wherein the body vessel is supported by body tissue;
   providing a tool body including a forceps having first and second opposable jaws coupled to first and second handles, respectively, the forceps supporting an elongated electrosurgical cutting electrode on the first jaw and a ground electrode on the second jaw;
   surgically dissecting a section of the body vessel from the body tissue and forming an opening in the body vessel to expose the vessel lumen
   applying the elongated electrosurgical cutting electrode to the surface of the vessel wall in substantially parallel alignment with the body vessel axis, the elongated electrosurgical cutting electrode having a predetermined cutting electrode length exceeding the cutting electrode width, the step of applying the elongated electrosurgical cutting electrode comprises inserting the first jaw through the vessel wall opening into the vessel lumen;
   applying the ground electrode in contact with the body of the patient comprising bring the first and second opposable jaws together; and
   applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

19. A method of making an elongated slit through a vessel wall and into a lumen of a body vessel, having a body vessel axis, of a patient comprising the steps of:
   obtaining access to a surface of the vessel wall, wherein the body vessel is supported by body tissue;
   providing a tool body including a forceps having first and second opposable jaws coupled to first and second handles, respectively, the forceps supporting a ground electrode on the first jaw and an elongated electrosurgical cutting electrode on the second jaw;
   surgically dissecting a section of the body vessel from the body tissue
   applying the ground electrode in contact with the body of the patient comprising applying the first jaw against one side of an outer surface of the vessel wall;
   applying the elongated electrosurgical cutting electrode to the surface of the vessel wall in substantially parallel alignment with the body vessel axis, the elongated electrosurgical cutting electrode having a predetermined cutting electrode length exceeding the cutting electrode width, the step of applying the elongated electrosurgical cutting electrode in contact with the surface of the vessel wall comprises bringing the second jaw against the other side of the outer surface of the vessel wall; and
   applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

20. A method of making an elongated slit through a vessel wall and into a lumen of a body vessel, having a body vessel axis, of a patient comprising the steps of:
   obtaining access to a surface of the vessel wall;
   applying a ground electrode in contact with the body of the patient;
   applying an elongated electrosurgical cutting electrode to the surface of the vessel wall in substantially parallel alignment with the body vessel axis, the elongated electrosurgical cutting electrode having a predetermined cutting electrode length exceeding the cutting electrode width;
   applying gripping force to the body vessel to compress and stabilize the body vessel from movement and to maintain the elongated electrosurgical cutting electrode in contact with the surface of the body vessel; and
   applying RF energy between the electrosurgical cutting electrode and the ground electrode at an energy level and for a duration sufficient to cut an elongated slit through the vessel wall where the elongated electrosurgical cutting electrode is applied to the surface of the vessel wall.

21. A method of creating an arteriotomy of the arterial wall of a coronary artery, having a coronary artery axis, of a patient into the lumen of the coronary artery comprising the steps of:
   obtaining access to a surface of the arterial wall of the coronary artery;
   applying a ground electrode in contact with the body of the patient;
   applying an elongated electrosurgical cutting electrode to the surface of the arterial wall of the coronary artery in substantially parallel alignment with the coronary artery axis, wherein the step of applying a ground electrode further comprises applying the ground electrode to the arterial wall in proximity with the elongated electrosurgical cutting electrode applied to the surface of the coronary artery; and
   applying RF energy between the electrosurgical cutting electrode and the ground electrode at an energy level and for a duration sufficient to cut an elongated slit through the arterial wall where the elongated electrosurgical cutting electrode is applied to the surface of the arterial wall.

22. A method of creating an arteriotomy of a source vessel wall of a patient into the lumen of the source vessel in preparation for a side-by-side anastomosis of a source vessel, having a source vessel axis, with a coronary artery of the patient comprising the steps of:
- obtaining access to a surface of the wall of the source vessel;
- applying a ground electrode in contact with the body of the patient;
- applying an elongated electrosurgical cutting electrode to the surface of the wall of the source vessel in substantially parallel alignment with the axis of the source vessel, wherein the step of applying a ground electrode further comprises applying the ground electrode to the wall of the source vessel in proximity with the elongated electrosurgical cutting electrode applied to the surface of the source vessel; and
- applying RF energy between the electrosurgical cutting electrode and the ground electrode at an energy level and for a duration sufficient to cut an elongated slit through the source vessel wall where the elongated electrosurgical cutting electrode is applied to the surface of the source vessel wall.

* * * * *